(12) United States Patent
Niles et al.

(10) Patent No.: US 6,797,461 B2
(45) Date of Patent: Sep. 28, 2004

(54) TRYPTASE SUBSTRATES AND ASSAY FOR TRYPTASE ACTIVITY USING SAME

(75) Inventors: Andrew L. Niles, Madison, WI (US); Mary Haak-Frendscho, Newark, CA (US); Jennifer L. Harris, San Diego, CA (US); Charles S. Craik, San Francisco, CA (US)

(73) Assignee: Promega Corporation, Madison, WI (US)

( * ) Notice: Subject to any disclaimer, the term of this patent is extended or adjusted under 35 U.S.C. 154(b) by 0 days.

(21) Appl. No.: 09/955,639

(22) Filed: Sep. 19, 2001

(65) Prior Publication Data

US 2002/0197661 A1 Dec. 26, 2002

Related U.S. Application Data

(60) Provisional application No. 60/244,013, filed on Oct. 27, 2000.

(51) Int. Cl.[7] .......................... C12Q 1/00; A61K 38/07; C07K 5/10
(52) U.S. Cl. .............................. 435/4; 435/23; 530/324; 530/330
(58) Field of Search ...................... 435/4, 23; 530/324, 530/330

(56) References Cited

U.S. PATENT DOCUMENTS

| | | | |
|---|---|---|---|
| 4,314,936 A | * 2/1982 | Yaron et al. ................. 530/331 |
| 4,390,528 A | 6/1983 | Naijar | |
| 4,409,141 A | 10/1983 | Noda et al. | |
| 5,391,705 A | 2/1995 | Neises et al. | |

FOREIGN PATENT DOCUMENTS

| | | |
|---|---|---|
| GB | 2 324 529 | 10/1998 |
| WO | 98/50579 | * 11/1998 |
| WO | WO 00/447323 | 8/2000 |
| WO | WO 01/94332 | 12/2001 |

OTHER PUBLICATIONS

Barbier, Bernard, et al., "Basic Polypeptides Accelerate the Hydrolysis of Ribonucleic Acids", *J.Am.Chem.Soc.*, vol. 110, No. 20, 1998, pp. 6880–6683.
Backes, B. J., Harris, J. L., Leonetti, F., Craik, C. S., and Ellman, J. A. (2000) *Nature Biotechnology* 18(2), 187–193.
Besson, T., Joseph, B., Moreau, P., Viaud, M. C., Coudert, G. & Guillaumet, G. (1992) *Heterocycles* 34, 273–291.
Gill, S. C. and Von Hippel, P. H. (1989) *Anal. Biochem.* 182, 319–326.
Harris, J., Backes, B., Leonetti, F., Mabrus, S., Ellman, J., and Craik, C. (2000) *Proceedings of the National Academy of Sciences* 97(14), 7754–7759.
Harris, J. L., Peterson, B. P., Hudig, D., Thornberry, N. A., and Craik, C. S. (1998) *Journal of Biological Chemistry* 273 (42), 27364–73.
Huang, C., Li, L., Krilis, S., Chanasyk, K., Tang, Y., Li, Z., Hunt, J., and Stevens, R. (1999) *Journal of Biological Chemistry* 274(28), 19670–19676.
Jameson, G., Roberts, DV, Adams, RW, Kyle, WS, Elmore, DT. (1973) *Biochemical Journal* 131(1), 107–17.
Kanaoka, Y., Kobayashi, A., Sato, E., Nakayama, H., Ueno, T., Muno, D. & Sekine, T. (1984) *Chem. Pharm. Bull.* 32, 3926–3933.
Lee, D., et al., (1999) *Bioorganic and Medicinal Chemistry Letters* 9:1667–72.
Niles, A. L., Maffitt, M., Haak–Frendscho, M., Wheeless, C. J., and Johnson, D. A. (1998) *Biotechnology and Applied Biochemistry* 28(Pt 2)), 125–31.
Ostresh et al., (1994) *Biopolymers* 34:1681–1689.
Pallaoro, M., Fejzo, M., Shayesteh, L., Blount, J., and Caughey, G. (1999) *Journal of Biological Chemistry* 274(6), 3355–3362.
Rano, T.A., et al, (1997) *Chemistry* and *Biology* 4:149–55.
Schwartz, L., Lewis, R., and Austen, K. (1981) *Journal of Biological Chemistry* 256, 11939–11943.
Stack, M., and Johnson, D. (1994) *Journal of Biological Chemistry* 269(13), 9416–9419.
Tam, E., and Caughey, G. (1990) *Am. J. Respir. Cell Mol. Biol.* 3, 27–32.

* cited by examiner

Primary Examiner—Bennett Celsa
(74) Attorney, Agent, or Firm—Joseph T. Leone, Esq.; DeWitt Ross & Stevens S.C.

(57) ABSTRACT

The invention is directed to synthetic polypeptide substrates for tryptase enzymes and assays for tryptase activity that utilize the synthetic polypeptide substrates. The preferred synthetic polypeptide substrates are tetramers of the formula P4-P3-P2-P1, wherein the substrate is selected from the group consisting of P-R-N-K (SEQ. ID. NO: 2), P-K-N-K (SEQ. ID. NO: 3), P-R-N-R (SEQ. ID. NO: 4), P-K-N-R (SEQ. ID. NO: 5), P-A-N-K (SEQ. ID. NO: 6), and P-R-T-K (SEQ. ID. NO: 7).

35 Claims, 15 Drawing Sheets

THE SHECTER & BERGER NOMENCLATURE

Fluorometric Tryptase Activity Assay Using Ac-PRNK-ACC in Spiked Assay Buffer

SEQUENCE LISTING

```
<160> NUMBER OF SEQ ID NOS: 23

<210> SEQ ID NO 1
<211> LENGTH: 4
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Xaa at position 2 is Arg (R) or Lysine (K)
<220> FEATURE:
<221> NAME/KEY: MISC_FEATURE
<222> LOCATION: (3)..(3)
<223> OTHER INFORMATION: Xaa at position 3 is any amino acid
<220> FEATURE:
<221> NAME/KEY: MISC_FEATURE
<222> LOCATION: (4)..(4)
<223> OTHER INFORMATION: Xaa at position 4 is Arg (R) or Lys (K)
```

-continued

```
<400> SEQUENCE: 1

Pro Xaa Xaa Xaa
1

<210> SEQ ID NO 2
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 2

Pro Arg Asn Lys
1

<210> SEQ ID NO 3
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 3

Pro Lys Asn Lys
1

<210> SEQ ID NO 4
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 4

Pro Arg Asn Arg
1

<210> SEQ ID NO 5
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 5

Pro Lys Asn Arg
1

<210> SEQ ID NO 6
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 6

Pro Ala Asn Lys
1

<210> SEQ ID NO 7
<211> LENGTH: 4
<212> TYPE: PRT
<213> ORGANISM: Artificial Sequence
<220> FEATURE:
<223> OTHER INFORMATION: Synthetic polypeptide
```

```
<400> SEQUENCE: 7

Pro Arg Thr Lys
1

<210> SEQ ID NO 8
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 8

Pro Arg Phe Lys
1

<210> SEQ ID NO 9
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 9

Thr Arg Leu Arg
1

<210> SEQ ID NO 10
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 10

Ser Lys Gly Arg
1

<210> SEQ ID NO 11
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 11

Pro Asn Asp Lys
1

<210> SEQ ID NO 12
<211> LENGTH: 4
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: P at position 1 is modified to contain
      an N-terminal acetyl group
<220> FEATURE:
<221> NAME/KEY: MOD_RES
<222> LOCATION: (4)..(4)
<223> OTHER INFORMATION: K at position 4 is modified to contain a
      C-terminal 7-amino-4-car bamoylmethyl-coumarin group

<400> SEQUENCE: 12

Pro Arg Asn Lys
1
```

<210> SEQ ID NO 13
<211> LENGTH: 4
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: P at position 1 is modified to include an
      N-terminal acetyl group
<400> SEQUENCE: 13

Pro Arg Asn Lys
1

<210> SEQ ID NO 14
<211> LENGTH: 4
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: P at position 1 is modified to include an
      N-terminal acetyl group
<220> FEATURE:
<221> NAME/KEY: MOD_RES
<222> LOCATION: (4)..(4)
<223> OTHER INFORMATION: K at position 4 is modified to include
      a C-terminal chloromethyl ketone group

<400> SEQUENCE: 14

Pro Arg Asn Lys
1

<210> SEQ ID NO 15
<211> LENGTH: 4
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: P at position 1 is modified to include an
      N-terminal acetyl group
<220> FEATURE:
<221> NAME/KEY: MOD_RES
<222> LOCATION: (4)..(4)
<223> OTHER INFORMATION: K at position 4 is modified to include a
      C-terminal 7-amino-4-car bamoylmethyl-coumarin group

<400> SEQUENCE: 15

Pro Arg Asn Lys
1

<210> SEQ ID NO 16
<211> LENGTH: 4
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: P at position 1 is modified to include
      an N-terminal acetyl group
<220> FEATURE:
<221> NAME/KEY: MOD_RES
<222> LOCATION: (4)..(4)

```
<223> OTHER INFORMATION: K at position 4 is modified to
      include a C-terminal 7-amino-4-car
      bamoylmethyl-coumarin group

<400> SEQUENCE: 16

Pro Arg Thr Lys
1

<210> SEQ ID NO 17
<211> LENGTH: 4
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: P at position 1 is modified to
      include an N-terminal acetyl group
<220> FEATURE:
<221> NAME/KEY: MOD_RES
<222> LOCATION: (4)..(4)
<223> OTHER INFORMATION: K at position 4 is modified to
      include a C-terminal 7-amino-4-car
      bamoylmethyl-coumarin group

<400> SEQUENCE: 17

Pro Arg Asn Arg
1

<210> SEQ ID NO 18
<211> LENGTH: 4
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: N-METHYLATION

<400> SEQUENCE: 18

Pro Arg Asn Lys
1

<210> SEQ ID NO 19
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 19

Pro Arg Phe Lys
1

<210> SEQ ID NO 20
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 20

Ile Arg Ser Lys
1
```

```
<210> SEQ ID NO 21
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 21

Ser Lys Gly Arg
1

<210> SEQ ID NO 22
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 22

Phe Arg Thr Lys
1

<210> SEQ ID NO 23
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 23

Ile Lys Thr Lys
1
```

TRYPTASE SUBSTRATES AND ASSAY FOR TRYPTASE ACTIVITY USING SAME

PRIORITY

Priority is hereby claimed to provisional application Serial No. 60/244,013, filed Oct. 27, 2000, the entire contents of which is incorporated herein by reference.

This invention was made with United States government support awarded by the National Institutes of Health under grant no. CA72006. The United States has certain rights in this invention.

FIELD OF THE INVENTION

The invention relates to assays to detect tryptase activity and polypeptide tryptase substrates utilized in the assay.

BIBLIOGRAPHY

Complete bibliographic citations to the references noted herein are included in the Bibliography section, immediately preceding the claims.

DESCRIPTION OF THE RELATED ART

Mast cells are distributed on all epithelial and mucosal surfaces of the body. In addition to being found in mucous membranes of the respiratory and gastrointestinal tract, mast cells are also located near blood vessels in connective tissue. Mast cells play an important role in innate and acquired immune responses through the release of dense granules upon activation. The major component of mast cell secretory granules is serine proteases (Schwartz, L., et al.).

Human β-tryptase is the most abundant and unique member of the serine protease family. Although β-tryptase has uncertain physiological functions, it has been implicated as an effector in a plethora of human allergic and pathophysiological conditions, including asthma, arteriosclerosis, cancer, otitis media, arthritis, interstitial cystitis, rhinitis, dermatitis, and other deep organ diseases. Its prominent role in tissue remodeling and angiogenesis is suggestive of potentially beneficial physiological processes. There are at least three proteolytically active isoformns of tryptase present in mast cells, βI-tryptase, βII-tryptase, and βIII-tryptase. These tryptase isoforms are secreted as catalytically active tetramers (~135 kD) that are resistant to inactivation by plasma inhibitors.

The β-tryptase enzyme has been recently crystallized, and the structure suggests that the association of the tryptase subunits into the native tetramer results in a stereospecific admission of potential substrates to the active site of each subunit. Although several in vitro studies have identified multiple substrates for tryptase, including neuropeptides, fibrinogen, stromelysin, pro-urokinase, prothrombin, and protease activated receptor-2, the physiologically relevant in vivo target of β-tryptases's serine protease activity has eluded discovery.

Human chromosome 16 encodes at least four homologous, yet distinct, tryptase genes, designated α-, βI-, β11-, and βIII-tryptase (Pallaoro, M., et al.). As used herein the unmodified term "tryptase" shall be used to refer to all tryptase isoforms. Two β-tryptase isoforms share greater than 99% sequence identity, the βI- and βII-tryptases differing by only a single N-glycosylation site. It is not clear why so many highly similar tryptases are expressed by mast cells. One possibility is that they each perform different proteolytic functions that may be reflected in their substrate specificity preferences. Indeed, it has recently been shown that a single amino acid substitution between tryptase α and tryptase βII accounts for discrimination in substrate preference for the two enzymes (Huang, C., et al.).

It has been difficult to study β-tryptase and its physiological role because there are no suitable animal models for human allergies. Further, the human β-tryptases show little or no homology with the tryptases found in animals other than primates. Finally, isolating natural β-tryptase from human cadavers is a tedious and biohazardous undertaking. Only recently has recombinant, enzymatically-active tryptase become available through the work of the assignee of the present application, Promega Corporation of Madison, Wis., USA. (See co-pending and co-owned U.S. patent applications Ser. No. 09/598,982, filed Jun. 21, 2000, and Ser. No. 091079,970, filed 15 Apr. 1998, the entire contents of which are incorporated herein.)

During the past decade, clinicians have appreciated and reported the value of measuring released tryptase in making atopic diagnoses as well as when monitoring the course of mast cell-mediated disease. ("Atopic" being an umbrella term designating disease states characterized by symptoms produced upon exposure to an excitatory antigen or conditions such as asthma and other allergic reaction) β-tryptase may be detected in the serum of non-atopic "normal" individuals, and population serum levels are typically less than 1000 picograms of β-tryptase per milliliter of serum. Conversely, serum tryptase levels are markedly raised in atopic subjects. Too often however, immunological detection (i.e., ELISA, RIA, PCFIA, and related assays of tryptase) is fraught with poor sensitivity or availability (e.g., the Schwartz ELISA method) and the requisite need for expensive ancillary detection equipment. Except in cases of exaggerated mast cell burden or degranulation, such as occurs during mastocytosis or anaphylaxis, it has been difficult to establish non-atopic or remission baselines of tryptase.

Conventional methods of assaying for tryptase proteolytic activity are hampered by poor specificity. These methods use substrates that are only intended for the measurement of "trypsin-like" activity, particularly in purified tryptase preparations. For example, Benzoyl-Arg-paranitroaniline (trypsin), Tosyl-Gly-Pro-Arg-pNa (thrombin), Tosyl-Gly-Pro-Lys-pNa (plasmin), and Tosyl-Arg-Methyl-Ester exhibit cleavage upon contact by tryptase, but also are cleaved by other serine proteases. Because tryptase and related blood-borne serine proteases are able to cleave these substrates, they are of little value in ascertaining tryptase activity levels in complex biological samples.

SUMMARY OF THE INVENTION

The invention, which is defined by the claims set out at the end of this disclosure, is intended to solve at least some of the problems noted above.

A first embodiment of the invention is directed to an isolated polypeptide comprising in amino to carboxy order P4-P3-P2-P1, wherein P4 is Proline ("P"), P3 is Arginine ("R") or Lysine ("K"), P2 is any amino acid, and P1 is K or R (SEQ. ID. NO: 1). For amino acid abbreviations, see Table 1 below. These isolated polypeptides function as very specific substrates that can be cleaved by the action of tryptases.

A second embodiment of the invention is directed to a method of assaying activity of an enzymatically-active β-tryptase in a sample. The method comprises first contacting the sample with an isolated polypeptide comprising in amino to carboxy order P4-P3-P2-P1, where P4 is P, P3 is R or K, P2 is any amino acid, and βI is K or R (SEQ. ID. NO:

1). The isolated polypeptide also includes a detectable leaving group bound to P4-P3-P2-P1, and is amino-terminally blocked. The sample is contacted with the isolated polypeptide under conditions wherein an amount of the detectable leaving group is cleaved from P4-P3-P2-P1 upon action of β-tryptase present in the sample. The amount of detectable leaving group cleaved from the polypeptide is then quantified to give an indication of the extent of tryptase activity in the sample.

In the preferred embodiment of the method, the sample is contacted with an isolated polypeptide comprising in amino to carboxy order P4-P3-P2-P1, wherein P4 is acetylated, and wherein P4-P3-P2-P1 is selected from the group consisting of P-R-N-K (SEQ. ID. NO: 2), P-K-N-K (SEQ. ID. NO: 3), P-R-N-R (SEQ. ID. NO: 4), P-K-N-R (SEQ. ID. NO: 5), P-A-N-K (SEQ. ID. NO: 6), and P-R-T-K (SEQ. ID. NO: 7) (wherein asparagine is "N" and threonine is "T"), and further wherein a fluorogenic leaving group comprising 7-amino-4-carbamoylmethyl- coumarin is bound via an amide bond to P4-P3-P2-P1 at a carboxy-terminus of P4-P3-P2-P1. Here, if the sample has any tryptase activity, such activity will produce a detectable fluorescent moiety. The fluorescence of the sample is then measured to determine whether it undergoes a detectable change in fluorescence, the detectable change being an indication of the activity of the enzymatically-active β-tryptase in the sample. The sample may be any sample suspected of containing tryptase activity, including whole blood, serum, plasma, urine, tears, lavage, tissue extract, conditioned media, etc.

A third embodiment of the invention is directed to a kit for analyzing samples for β-tryptase activity. The kit comprises an isolated polypeptide comprising, in amino to carboxy order, P4-P3-P2-P1, wherein P4 is P, P3 is R or K, P2 is any amino acid, and P1 is K or R (SEQ. ID. NO: 1), and wherein a detectable leaving group is covalently bound to P4-P3-P2-P1, with the isolated polypeptide being disposed in a suitable container. The kit may also contain P4-P3-P2-P1 with a serine protease reactive moiety. The kit may optionally contain a supply of recombinant tryptase to be used to generate a standard curve, as well as a supply of aprotinin or a functional equivalent thereof. It is much preferred that instructions for use of the kit accompany each kit.

As noted above, mast cells express at least four distinct tryptase genes: α, βI, βII, and βIII. It is currently unknown if these proteases perform the same or different functions. Based on the data presented herein, βI, and βII-tryptases have very similar P4 to P1 substrate preferences. This shared preference for peptide substrates likely extends to a shared preference for physiological substrates. Indeed, the optimal sequence for β-tryptase, P4=P, P3=R or K, P2=any amino acid, and P1=K or R, is found in many of the macromolecular substrates that have been shown, at least in vitro, to be cleaved by tryptase, which preferentially cleaves after R or K.

For example, activation of the plasminogen cascade resulting in the destruction of extracellular matrix for cellular extravasation and migration may be a function of tryptase activation of pro-urokinase plasminogen activator at the P4-P1 sequence of Pro-Arg-Phe-Lys (SEQ. ID. NO: 8) (Stack, M., and Johnson, D.). Vasoactive intestinal peptide, a neuropeptide that is implicated in the regulation of vascular permeability, is cleaved by tryptase mainly after the arginines at the Thr-Arg-Leu-Arg (SEQ. ID. NO: 9) sequence (Stack, M., and Johnson, D.). The G-protein coupled receptor, PAR-2, can be cleaved and activated by tryptase at Ser-Lys-Gly-Arg (SEQ. ID. NO: 10), whereas the thrombin activated receptor, PAR-1, is inactivated by tryptase after the site Pro-Asn-Asp-Lys (SEQ. ID. NO: 11) (Jameson, G., et al.).

In the work leading to this invention, enzymatically-active βI- and βII-tryptases were heterologously expressed and purified in yeast to characterize the substrate specificity of each enzyme. Several positional scanning combinatorial tetrapeptide substrate libraries were used to dissect the primary and extended substrate specificity. Both enzymes have a strict primary preference for cleavage after the basic amino acids lysine and arginine, with only a slight preference for lysine over arginine. βI- and βII-tryptases share similar extended substrate specificity, preferring to cleave after P4-proline, P3-arginine or lysine, with P2 having some asparagine and threonine selectivity (N-preference, FIG. 3A).

It is shown herein that βI- and βII-tryptases have a defined primary substrate specificity (i.e., the residue at the P1 position) and a defined extended substrate specificity (i.e., the residues at the P4-P2 positions). The library profiles generated in developing the invention described and claimed herein indicate that the substrate specificity is similar for the two enzymes. Furthermore, single substrates were designed and assayed to test the extended substrate specificity requirements, thereby yielding sensitive and selective substrates for β-tryptases. Structural determinants of specificity were examined through the modeling of the optimized substrate into the active site of the tryptase structure. Finally, the specificity determined in this study correlates with the cleavage sites found in many of the characterized physiological substrates and may lead to the identification of additional substrates in both the immunity and pathology of βI- and βII-tryptases.

The invention described herein highlights the utility of using generalized positional scanning combinatorial peptide libraries to characterize functional similarities and differences between homologous enzymes, to generate sensitive and selective tryptase substrates and inhibitors, and to define a subset of potential physiological tryptase substrates.

The objects and advantages of the invention will appear more fully from the following detailed description of the preferred embodiment of the invention made in conjunction with the accompanying drawings.

DETAILED DESCRIPTION OF THE INVENTION

Abbreviations and Definitions:

To provide a clear and consistent understanding of the specification and claims, the following definitions are used herein. Terms not expressly described have their standard meaning as understood by those skilled in the art.

ACC—Refers to 7-amino-4-carbamoylmethyl-coumarin.

Amino acids—Abbreviations for the amino acids are provided in Table 1.

TABLE 1

| Amino Acid | Three-letter Abbreviation | One-letter Symbol |
|---|---|---|
| Alanine | Ala | A |
| Arginine | Arg | R |
| Asparagine | Asn | N |
| Aspartic acid | Asp | D |
| Asparagine or Aspartic acid | Asx | B |
| Cysteine | Cys | C |
| Glutamine | Gln | Q |
| Glutamic Acid | Glu | E |
| Glutamine or Glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |

TABLE 1-continued

| Amino Acid | Three-letter Abbreviation | One-letter Symbol |
|---|---|---|
| Tyrosine | Tyr | Y |
| Valine | Val | V |

Enzymatically-active tryptase—As applied to the expression of heterologous proteins from a genetically-engineered host cell, a protein is enzymatically active when it does not require post-expression or post-isolation chemical processing such as artificial cleavage of a secretion signal peptide or artificial glycosylation in order for the expressed/isolated protein to have the desired activity. Proteolytic tryptase must be correctly formed into the tetrameric form to be enzymatically active.

Fmoc—Refers to 9-fluorenylmethoxycarbonyl.

Genetic Engineering—Many of the steps noted below for the manipulation of DNA, including digesting with restriction endonucleases, amplifying by PCR, hybridizing, ligating, separating and isolating by gel electrophoresis, transforming cells with heterologous DNA, selecting successful transformants, and the like, are well known and widely practiced by those skilled in the art and are not extensively elaborated upon herein. Unless otherwise noted, the DNA protocols utilized herein are described in *Sambrook, Fritsch, and Maniatis* (1989).

TRYPTASE SUBSTRATES

Figure 1:
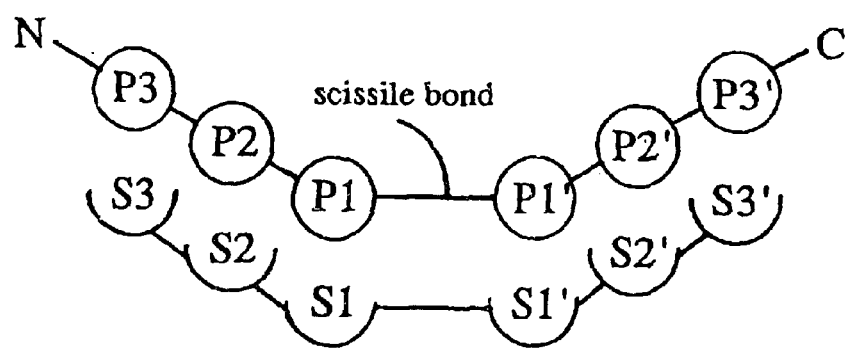
FIG. 1 is a depiction of the standard nomenclature for substrate amino acid preferences relative to the scissile bond cleavage site. Adopted from Schechter, I and Berger, A, (1967) "On the size of the active site in proteases." *Biochem. Biophys. Res. Com.*, 27, 157–162.

The substrate specificity of heterologously expressed human βI- and βII-tryptases was defined using multiple positional scanning synthetic combinatorial tetrapeptide libraries (PS-SCL). FIG. 1 illustrates the standard nomenclature for substrate amino acid preference relative to scissile bond cleavage site. The amino acids on the amino-terminus of the substrate are denoted Pn, Pn-1, . . . P2, P1. The amino acids on the carboxy-terminus of the substrate are denoted P1', P2', . . . ,Pm-1'. Thus, substrates written in a P4-P3-P2-P1 format are from the amino-terminus to the carboxy-terminus. Amide bond hydrolysis occurs between P1 and P1'. Sn, Sn-1, . . . , S2, S1, S1', S2, . . . Sm-1', Sm' denotes the corresponding enzyme binding sites.

A Positional Scanning-Synthetic Combinatorial Substrate Library (PS-SCL) was used to identify the extended substrate specificity of human recombinant βI- and βII-tryptase at the P1-P4 positions relative to the scissile bond cleavage site. The information from these libraries was then used to design preferred, optimized fluorogenic substrates, Acetyl-Prolyl-Arginyl-Asparaginyl-Lysyl-aminoacetamide coumarin (Ac-PRNK-AAC) (SEQ. ID. NO: 12) being most preferred. As described herein, this optimized substrate can be used to detect minute concentrations of active tryptase in complex biological fluids. This substrate can also act as an activity reporter in high-throughput screening applications. The information from the PS-SCL also was used to design a preferred specific active-site inhibitor, Acetyl-Prolyl-Arginyl-Asparaginyl-Lysyl-chloromethyl ketone (Ac-PRNK-CMK) (SEQ. ID. NO: 14).

Materials:

DNA modifying enzymes were purchased from Promega Corporation (Madison, Wis.). Heparin and other biochemicals were purchased from Sigma (St. Louis, Mo.).

Positional Scanning Synthetic Combinatorial Libraries:

ACC-Resin Synthesis:

7-Fmoc-aminocoumarin-4-acetic acid was prepared by treating 7-aminocoumarin-4-acetic acid (Kanaoka, Y., et al., Besson, T., et al.) with Fmoc-Cl. 7-Aminocoumarin-4-acetic acid (10.0 g, 45.6 mmol) and H$_2$O (228 ml) were mixed. NaHCO$_3$ (3.92 g, 45.6 mmol) was added in small portions followed by the addition of acetone (228 ml). The solution was cooled with an ice bath, and Fmoc-Cl (10.7 g, 41.5 mmol) was added with stirring over the course of 1 h. The ice bath was removed and the solution was stirred overnight.

The acetone was removed with rotary evaporation and the resulting gummy solid was collected by filtration and washed with several portions of hexane. The material was dried over P$_2$O$_5$ to give 14.6 g (80%) of cream-colored solid. $^1$H NMR (400 MHz): 3.86 (s, 2), 4.33 (t, 1, J=602), 4.55 (d, 2, J=6.2), 6.34 (s, 1), 7.33–7.44 (m, 5), 7.56 (s, 1), 7.61 (d, 1, J=8.6), 7.76 (d, 2, J=7.3), 7.91 (d, 2, J=7.4), 10.23 (s, 1), 12.84 (s, 1). $^{13}$C NMR (101 MHz): 37.9, 47.4, 66.8, 67.2, 105.5, 114.6, 115.3, 121.1, 125.9, 126.9, 128.0, 128.6, 141.6, 143.6, 144.5, 150.7, 154.1, 154.8, 160.8, 171.4.

ACC-resin was prepared by condensation of Rink Amide AM resin with 7-Fmoc-aminocoumarin-4-acetic acid. Rink Amide AM resin (21 g, 17 mmol) was solvated with DMF (200 ml). The mixture was agitated for 30 min and filtered with a filter cannula, whereupon 20% piperidine in DMF (200 ml) was added. After agitation for 25 min, the resin was filtered and washed with DMF (3 times, 200 ml each). 7-Fmoc-aminocoumarin-4-acetic acid (15 g, 34 mmol), HOBt (4.6 g, 34 mmol), and DMF (150 ml) were added, followed by DICI (5.3 ml, 34 mmol). The mixture was agitated overnight, filtered, washed (DMF, three times with 200 ml; tetrahydrofuran, three times with 200 ml; MeOH, three times with 200 ml), and dried over P$_2$O$_5$. The substitution level of the resin was 0.58 mmol/g (>95%) as determined by Fmoc analysis (Harris et al., (2000)).

P1-Substituted ACC-Resin Synthesis:

Fmoc-ACC-resin (100 mg, 0.058 mmol) was added to 20 reaction vessels of an Argonaut Quest 210 Organic Synthesizer and solvated with DMF (2 ml). The resin was filtered and 20% piperidine in DMF (2 ml) was added to each vessel. After agitation for 25 min, the resin was filtered and washed with DMF (three times with 2 ml). An Fmoc-amino acid (0.29 mmol), DMF (0.7 ml), collidine (76 µl, 0.58 mmol), and HATU (110 mg, 0.29 mmol) were added to the designated reaction vessel, followed by agitation for 20 h. The resins were then filtered, washed with DMF (three times with 2 ml), and subjected a second time to the coupling conditions. A solution of AcOH (40 µl, 0.70 mmol), DICI (110 µl, 0.70 mmol), and nitrotriazole (80 mg, 0.70 mmol) in DMF (0.7 ml) was added to each of the reaction vessels, followed by agitation for 24 h. The resins were filtered, washed (DMF, three times with 2 ml; tetrahydrofuran, three times with 2 ml; MeOH, three times with 2 ml), and dried over P$_2$O$_5$. The substitution level of each resin was determined by Fmoc analysis Bunin (1998).

P1-Diverse Library Synthesis:

Individual P1-substituted Fmoc-amino acid ACC-resin (25 mg, 0.013 mmol) was added to wells of a MultiChem 96-well reaction apparatus. The resin-containing wells were solvated with DMF (0.5 ml). After filtration, a 20% piperidine in DMF solution (0.5 ml) was added, followed by agitation for 30 min. The wells of the reaction block were filtered and washed with DMF (three times with 0.5 ml). To introduce the randomized P2 position, an isokinetic mixture (Ostresh et al.) of Fmoc-amino acids (4.8 mmol, 10 eq per well; Fmoc-amino acid, mol %: Fmoc-Ala-OH, 3.4; Fmoc-Arg(Pbf)-OH, 6.5; Fmoc-Asn(Trt)-OH, 5.3; Fmoc-Asp(O-t-Bu)-OH, 3.5; Fmoc-Glu(O-t-Bu)-OH, 3.6; Fmoc-Gln(Trt)-OH, 5.3; Fmoc-Gly-OH, 2.9; Fmoc-His(Trt)-OH, 3.5; Fmoc-Ile-OH, 17.4; Fmoc-Leu-OH, 4.9; Fmoc-Lys(Boc)-OH, 6.2; Fmoc-Nle-OH, 3.8; Fmoc-Phe-OH, 2.5; Fmoc-Pro-OH, 4.3; Fmoc-Ser(O-t-Bu)-OH, 2.8; Fmoc-Thr(O-t-Bu)-OH, 4.8; Fmoc-Trp(Boc)-OH, 3.8; Fmoc-Tyr(O-t-Bu)-OH, 4.1; Fmoc-Val-OH, 11.3) was preactivated with DICI (390 µl, 2.5 mmol), and HOBt (340 mg, 2.5 mmol) in DMF (10 ml). The solution (0.5 ml) was added to each of the wells. The reaction block was agitated for 3 h, filtered, and washed with DMF (three times with 0.5 ml). The randomized P3 and P4 positions were incorporated in the same manner. The Fmoc of the P4 amino acid was removed and the resin was washed with DMF (three times with 0.5 ml) and treated with 0.5 ml of a capping solution of AcOH (150 µl, 2.5 mmol), HOBt (340 mg, 2.5 mmol), and DICI (390 µl, 2.5 mmol) in DMF (10 ml). After 4 h of agitation, the resin was washed with DMF (three times with 0.5 ml) and CH$_2$Cl$_2$ (three times with 0.5 ml), and treated with a solution of 95:2.5:2.5 TFA/TIS/H2O. After incubation for 1 h the reaction block was opened and placed on a 96-deep-well titer plate and the wells were washed with additional cleavage solution (twice with 0.5 ml). The collection plate was concentrated, and the material in the substrate-containing wells was diluted with EtOH (0.5 ml) and concentrated twice. The contents of the individual wells were lyophilized from CH$_3$CN/H$_2$O mixtures. The total amount of substrate in each well was conservatively estimated to be 0.0063 mmol (50%) on the basis of yields of single substrates.

P1-Fixed Library Synthesis:

Multigram quantities of P1-substituted ACC-resin can be synthesized by the methods described. Three libraries with the P1 position fixed as Lys, Arg, or Leu were prepared. Fmoc-amino acid-substituted ACC resin (25 mg, 0.013 mmol, of Lys, Arg, or Leu) was placed in 57 wells of a 96-well reaction block: three sublibraries denoted by the second fixed position (P4, P3, P2) of 19 amino acids (cysteine was omitted and norleucine was substituted for methionine). Synthesis, capping, and cleavage of the substrates were identical to those described in the previous section, with the exception that for P2, P3, and P4 sublibraries, individual amino acids (5 eq of Fmoc-amino acid monomer, 5 eq of DICI, and 5 eq of HOBt in DMF), rather than isokinetic mixtures, were incorporated in the spatially addressed P2, P3, or P4 positions.

Synthesis of Single Substrates:

Substrates in the positional scanning synthetic combinatorial libraries, Ac-PRNK-ACC (SEQ. ID. NO: 12), Ac-PANK-ACC (SEQ. ID. NO: 15), Ac-PRTK-ACC (SEQ. ID. NO: 16), and Ac-PRNR-ACC (SEQ. ID. NO: 17) were prepared as previously described; see Harris, J., et al. (2000), incorporated herein. The details of the synthesis follow immediately.

Single substrates for kinetic analysis were prepared by the methods described above. The unpurified products were subjected to reversed-phase preparatory HPLC followed by lyophilization.

Fluorescence Properties of ACC:

The fluorescence of free ACC and peptidyl-derivatized ACC was detected on a Spex fluorimeter thermostated to 25° C. Excitation wavelengths of 300–410 nm, 5-nm intervals, were used with emission wavelengths of 410–500 nm, 5-nm intervals, to determine optimal excitation and emission parameters.

Enzymatic Assay of Library:

The enzymatic assay of the library was performed as is described in Harris et al. (2000). The concentration of proteolytic enzymes was determined by absorbance measured at 280 nm (Gill, S. C. & von Hippel, P. H.). The proportion of catalytically active thrombin, plasmin, trypsin, uPA, tPA, and chymotrypsin was quantified by active-site titration with 4-methylumbelliferyl p-guanidinobenzoate (MUGB) or methylumbelliferyl p-trimethylammoniocinnamate chloride (MUTMAC) (Jameson, G. W., et al.).

Substrates from the positional scanning-synthetic combinatorial libraries (PS-SCLs) were dissolved in DMSO. Approximately $1.0 \times 10^{-9}$ mol of each P1-Lys, P1-Arg, or P1-Leu sublibrary (361 compounds) was added to 57 wells of a 96-well Microfluor plate (Dynex Technologies, Chantilly, Virginia) for a final concentration of 0.1 $\mu$M. Approximately $1.0 \times 10^{-10}$ mol of each P1-diverse sublibrary (6,859 compounds) was added to 20 wells of a 96-well plate for a final concentration of 0.01 $\mu$M in each compound.

Hydrolysis reactions were initiated by the addition of enzyme (0.02–100 nM) and monitored fluorimetrically with a Perkin-Elmer LS50B luminescence spectrometer, with excitation at 380 nm and emission at 450 nm or 460 nm. Assays of the serine proteases were performed at 25° C. in a buffer containing 50 mM Tris at pH 8.0, 100 mM NaCl, 0–5 mM CaCl2, 0.01% Tween-20, and 1% DMS0 (from substrates). Assay of the cysteine proteases, papain and cruzain, was performed at 25° C. in a buffer containing 100 mM sodium acetate at pH 5.5, 100 mM NaCl, 5 mM DTT, 1 mM EDTA, 0.01% Brij-35, and 1% DMSO (from substrates).

Single Substrate Kinetic Assays:

βI- and βII-tryptase concentrations ranged from 5 nM to 15 nM. The final concentration of substrate ranged from 5 $\mu$M to 200 $\mu$M; the concentration of DMSO in the assay was less than 5%. Hydrolysis of ACC substrates was monitored fluorometrically with an excitation wavelength of 380 nm and an emission wavelength of 460 nm on a Fluoromax-2 spectrofluorimeter.

β-II tryptase gene construction:

The pPIC9-Hu Try (human-βI tryptase plasmid) (Niles et al.) was generated as is described in co-pending and co-owned U.S. patent applications Ser. No. 09/598,982, filed Jun 21, 2000.

Expression and Purification:

Recombinant human βI- and βII-tryptases were expressed and purified as previously described (Niles, A. et al., U.S. patent application Ser. No. 09/598,982, filed Jun. 21, 2000, and U.S. patent application Ser. No. 09/079,970, filed Apr. 15, 1998). Briefly, pPIC9-Hu Try/N113K was linearized by Sac I digestion and transformed into the GS115 strain of Pichiapastoils (Pichiapastotis Expression System, Invitrogen, San Diego, Calif.). A tryptase-expressing clone was isolated and used for large-scale expression by fermentation in buffered minimal methanol complex media with 0.5 mg/ml heparin. Secreted mature βI- and βII-tryptases were purified to homogeneity using a two-column affinity chromatography procedure known to the art. The enzymes were suspended in a final storage buffer containing 2M NaCl and 10 mM MES, pH 6.1.

The proportion of catalytically active βI- and βII-tryptases was quantitated by active-site titration with 4-methylumbelliferyl p-guanidinobenzoate (MUGB) (Jameson, G., et al.). Briefly, fluorescence was monitored, with excitation at 360 nm and emission at 450 nm, upon addition of enzyme to MUGB. The concentration of enzyme was determined from the increase in fluorescence based on a standard concentration curve.

Positional scanning synthetic combinatorial library screening:

Preparation and screening of the positional scanning synthetic combinatorial library (PS-SCL) was carried out as described above (Harris, J., et al. (2000), Backes, B. J., et al.). The concentration of each of the 361 substrates per well in the P1-Lysine and P1-Arginine libraries was 0.25 $\mu$M, the concentration of the 6859 compounds per well in the P1-Diverse library was 0.013 $\mu$M. Enzyme activity of the PS-SCL was assayed in 100 mM hydroxyethylpiperazine-N'-2-ethanesulfonic acid (HEPES) pH 7.5, 10% glycerol, and 0 or 0.1 mg/ml heparin at excitation and emission wavelengths of 380 nm and 450 nm respectively.

Single substrate kinetic analysis:

Tryptase activity was monitored at 30° C. in assay buffer containing 100 mM HEPES, pH 7.5, 10% w/v glycerol, and 0.1 mg/ml heparin. Substrate stock solutions were prepared in DMSO. The final concentration of substrate ranged from 5 $\mu$M to 2000 $\mu$M, the concentration of DMSO in the assay was less than 5%. Tryptase concentration was 5 nM.

Fluorogenic Compounds:

Fluorogenic compounds are of use as probes for an array of applications, including structural elucidation of materials, substrate specificity of enzymes, hybridization of nucleic acids, substrate transformation, digestion or degradation of biomolecules, such as peptides, nucleic acids, saccharides, and the like. The present invention provides a solid support, which allows for the conjugation of a fluorogenic moiety to compounds of different types, which are synthesized on the solid support of the invention. A preferred solid support is a resin, although any other solid support, such as a plate, can be used.

The present invention also provides a fluorogenic peptide comprising a fluorogenic leaving group covalently bound to a peptide sequence P4-P3-P2-P1 at a carboxy-terminus of P4-P3-P2-P1. Preferably, the bond is an amide bond. The leaving group of the invention is exemplified by 7-amino-4-carbamoylmethyl-coumarin (ACC).

In an illustrative embodiment, using Fmoc-synthesis protocols, all 20 proteinogenic amino acids can be directly coupled to the support bound ACC-leaving group to provide general sets of substrates for analyzing protease substrate specificity. The versatility of the solid-phase synthesis strategy allows for substrate arrays. (Lee, D., et al., (1999)) and positional scanning libraries (Rano, T. A., et al, (1997)) of any configuration to be rapidly prepared. The substrate specificity of numerous representative serine and cysteine proteases were profiled to show the utility and generality of libraries generated by the ACC method.

The fluorogenic polypeptides of the invention preferably have a peptide sequence that includes at least one peptide bond cleavable by tryptase. Cleaving the peptide bond preferably releases the fluorogenic leaving group from the peptide.

Hydrolysis of ACC substrates was monitored fluorometrically with an excitation wavelength of 380 nm and emission wavelength of 450 nm on a Fluoromax-2 spectrofluorimeter. The amino-terminus of each polypeptide was acetylated.

Compound Libraries:

A library of fluorogenic polypeptides was created. The library is used to screen the substrate specificity of tryptase. Libraries in a positional or ordered array are preferred. Such libraries permit the identification of peptides, or other compounds, that are associated with zones of activity located during screening the library. Specifically, the library can be ordered so that the position of the peptide on the array corresponds to the identity of the peptide. Thus, once an assay has been carried out, and the position on the array determined for an active peptide, the identity of that peptide can be easily ascertained.

Fluorogenic Polypeptide:

In a preferred embodiment, the invention provides an isolated polypeptide including in amino to carboxy order P4-P3-P2-P1, wherein P4 is P, P3 is R or K, P2 is any amino acid, and P1 is K or R (SEQ. ID. NO: 1). The polypeptide is preferably acetylated and includes a fluorogenic leaving group that is covalently bound to P4-P3-P2-P1 at a carboxy-terminus of P4-P3-P2-P1. Preferably, the fluorogenic leaving group is bound via an amide bond. A preferred fluorogenic leaving group is 7-amino-4-carbamoylmethyl-coumarin. Thus, a preferred polypeptide is Ac-PRNK-ACC (SEQ. ID. NO: 12).

Tryptase Activity Assay:

In a preferred embodiment, the invention provides a method of assaying for the activity of an enzymatically-active β-tryptase in a sample. Sample that can be used in the assay include, but are not limited to, plasma, urine, tear, lavage, serum, or other bodily fluid clinical samples. The method includes steps of contacting the sample with an isolated polypeptide comprising in amino to carboxy order P4-P3-P2-P1. In this preferred embodiment, P4 is P, P3 is R or K, P2 is any amino acid, and P1 is K or R (SEQ. ID. NO: 1). P4 preferably is acetylated, and a fluorogenic leaving group is bound via an amide bond to P4-P3-P2-P1 at a carboxy-terminus of P4-P3-P2-P1. When the sample is contacted with the isolated polypeptide, the fluorogenic leaving group is cleaved from P4-P3-P2-P1 upon action of the β-tryptase. The sample can then be observed to determine whether it has undergone a detectable change in fluorescence, with the detectable change being an indication of the activity of the enzymatically-active β-tryptase in the sample.

Aprotinin Assays:

Aprotinin inhibits proteases other than β-tryptase. Thus, it can be added to a sample to reduce non-specific cleavage of the fluorogenic leaving group from P4-P3-P2-P1 by proteases other than β-tryptase. Accordingly, also provided is an assay that has the additional step of adding aprotinin to the sample to inhibit proteases other than β-tryptase.

Tryptase Polypeptide Inhibitor:

In another preferred embodiment of the invention provides an isolated polypeptide that inhibits tryptase. The isolated polypeptide includes in amino to carboxy order P4-P3-P2-P1, wherein P4 is P, P3 is R or K, P2 is any amino acid, and P1 is K or R (SEQ. ID. NO: 1). The polypeptide includes a serine protease reactive inhibitor moiety, such as chloromethyl ketone, that is linked to P1, and the P4 is acetylated.

Tryptase Inhibition:

The chloromethyl ketone-modified polypeptide described above can be used to inhibit β-tryptase. Thus, a method of inhibiting an enzymatically-active β-tryptase in a sample is provided that includes the step of contacting the sample with an isolated polypeptide comprising in amino to carboxy order P4-P3-P2-P1, wherein P4 is acetylated and wherein P1 is linked to a chloromethyl ketone. Preferably, P4 is P, P3 is R or K, P2 is any amino acid, and P1 is K or R (SEQ. ID. NO: 1). The contacting is done such that the isolated polypeptide interacts with the β-tryptase and thereby inhibits the β-tryptase. Optionally, the level of inhibition of the β-tryptase is observed.

Kits:

The present invention also provides for kits for analyzing samples for the activity of β-tryptase. The kits include one or more containers containing one or more fluorogenic polypeptides of the invention. The fluorogenic polypeptides may be provided in solution, lyophilized, or bound to a solid support. Thus, the kits may contain indicator solutions or indicator "dipsticks," blotters, culture media, and the like. The kits may also contain indicator cartridges (where the fluorogenic polypeptide is bound to a solid support) for use in automated tryptase activity detection.

The kits additionally may include an instruction manual that teaches a method of the invention and describes the use of the polypeptides of the kit. In addition, the kits may also include other reagents, buffers, various concentrations of enzyme inhibitors, stock enzymes (for the generation of standard curves, etc.), culture media, disposable cuvettes and the like to aid the detection of tryptase activity using the fluorogenic peptides of the present invention.

It will be appreciated that the kits may additionally, or alternatively, include any other indicators such as nucleic acid based indicators, oligosaccharide indicators, lipid indicators, Another kit containing an isolated polypeptide that inhibits β-tryptase is also provided.

Structural modeling of optimized substrate into tryptase active site:

The tryptase structure (PDB code 1aO1) was prepared for modeling by removing inhibitor and water molecules, adding hydrogens in Sybyl6.5, and assigning μMBER partial atomic charges. All four subunits of the tetramer were retained. Because the structure contains a covalent inhibitor, the catalytic Ser-195 was modeled to a geometry consistent with a noncovalent inhibitor by restoring the hydrogen bond with His-57. This was accomplished with a two-step torsional minimization in Sybyl6.5 (Tripos force field, eps=1r). In the first step the position of the Ser-195 hydroxyl hydrogen was minimized via torsion around the CCOH bond, and in the second step both the oxygen and hydrogen were minimized via torsion around the CCOH and CCCO (chi1) bonds. The coordinates of all atoms of the enzyme were held fixed for the remainder of the modeling.

The peptide backbone of Ac-PRNK-Nme (SEQ. ID. NO: 18) (i.e., the peptide was N-methylated) was modeled into the active site of the tryptase structure as follows. The structure of the P1-P3 portion of ovomucoid (complexed to chymotrypsin, PDB code 1 cho) was used as a template for the backbone configuration. This portion of the inhibitor was translated into the tryptase active site using least squares superposition of the protease active site residues 57, 102, 195, and 214-216 onto the corresponding residues of the tryptase "A" protomer. The peptide side chains were then truncated at C-beta, hydrogens, and AMBER charges were added (as above) and the configuration of the resultant (Ac-AAA-Nme) peptide was optimized with successive minimizations in the tryptase active site. Using DOCK4.0, the atoms of the scissile amide bond were minimized first, then successive rigid segments of the peptide were added (with torsional angles taken from the ovomucoid inhibitor) alternating with minimization. The minimizations included rigid and flexible degrees of freedom and were performed using the simplex algorithm with smaller initial step sizes than the default values (e.g., the maximum initial translation was 0.02 Angst.) and up to 500 iterations for each minimization. The scoring term, applied to both intermolecular and intramolecular atom pairs, includes the coulombic and van der Waals terms from AMBER, using an interatomic cutoff of 25 Angst. and eps.=4r. The peptide side chains (PRNK) (SEQ. ID. NO: 2) were then added, and the conformation of the P1-P3 side chains and the P4 proline were modeled with DOCK4.0 as in Lamb, M., et al., "Design, Docking, and Evaluation of Multiple Libraries Against Multiple Targets," *Proteins* (in press). Finally, ten independent minimizations were carried out, and the lowest-energy configuration was chosen.

EXAMPLES

The following examples are provided for illustrative purposes only. It is understood that the following examples do not limit the invention claimed herein in any way.

Example 1

Substrate Specificity of βI- and βII-Tryptases

Recombinant βI- and βII-tryptases were produced and secreted in Pichia pastoris as mature enzymes. The ability to produce active mature enzyme rather than the inactive, precursor zymogen is important for substrate specificity studies because it obviates the need to remove the pro-peptide through the addition of an activating protease, whose activity may complicate subsequent specificity studies. There is a single amino acid difference between βI- and βII-tryptases at position 113, an asparagine and a lysine respectively. Replacement of asparagine for lysine removes an N-linked glycosylation site in tryptase βII, making it contain one glycosylation site. The reduction in the number of glycosylation sites can be seen in the recombinant expression of both enzymes with βI-tryptase migrating as multiple glycosylated bands and βII-tryptase migrating as glycosylated and unglycosylated bands. The only difference seen in expression and purification of the two enzymes is the final yield of active enzyme with βI-tryptase expressing 10-fold more than βII-tryptase. The phenomena of reduced expression upon removal of the glycosylation site has been observed with other proteases and has been postulated to involve decreased stability or solubility of the enzyme without post-translational glycosylation (Harris, J. L., et al. (1998)).

Example 2

Substrate Specificities of βI- and βII-tryptases

Figure 2:
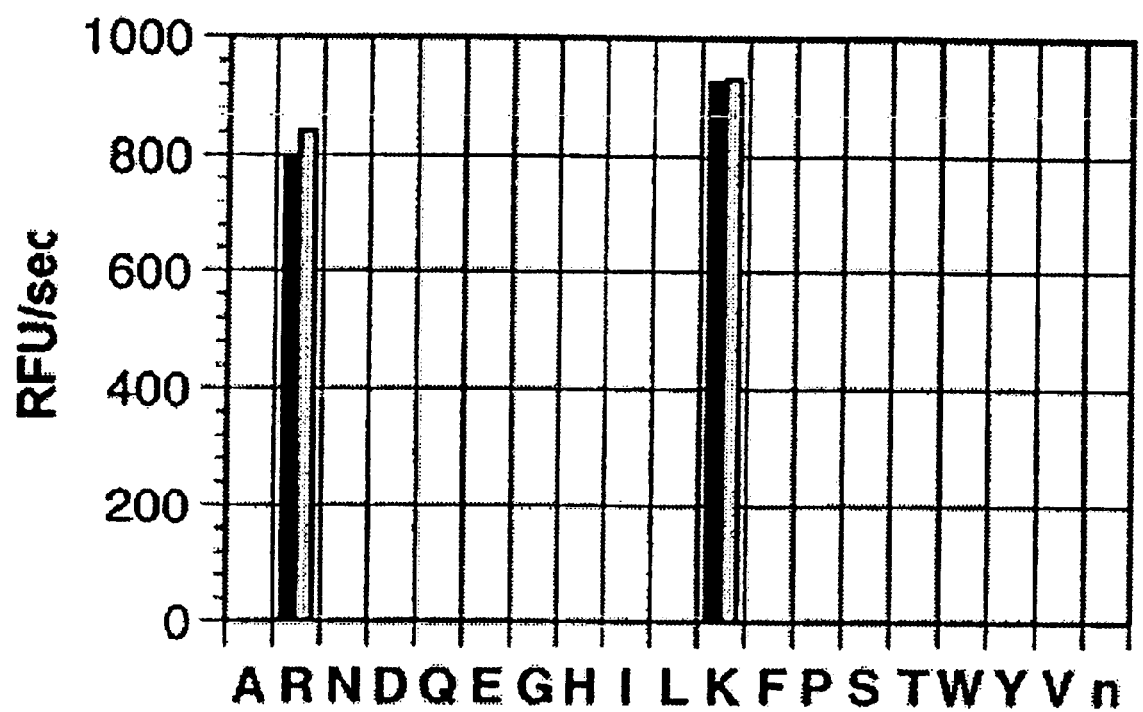
FIG. 2 shows an activity profile of tryptase against an ACC P1-diverse library. This P1-profile used recombinant human β-I tryptases and shows a strong preference for P1 being R or K.

To explore whether this single difference in glycosylation affects the substrate specificity of βI- and βII-tryptases, several combinatorial peptide libraries with fluorogenic leaving groups were utilized. The P1-position was first defined with a library in which each of the P1-amino acids in a tetrapeptide is held constant while the other three positions contain a equimolar mixture of 19 amino acids (cysteine was omitted and norleucine replaced methionine). Both βI- and βII-tryptases prefer cleaving after lysine over arginine with no other amino acids being accepted at this position (FIG. 2).

Example 3

Extended Substrate Specificities of βI- and βII-tryptases

Figure 3A:
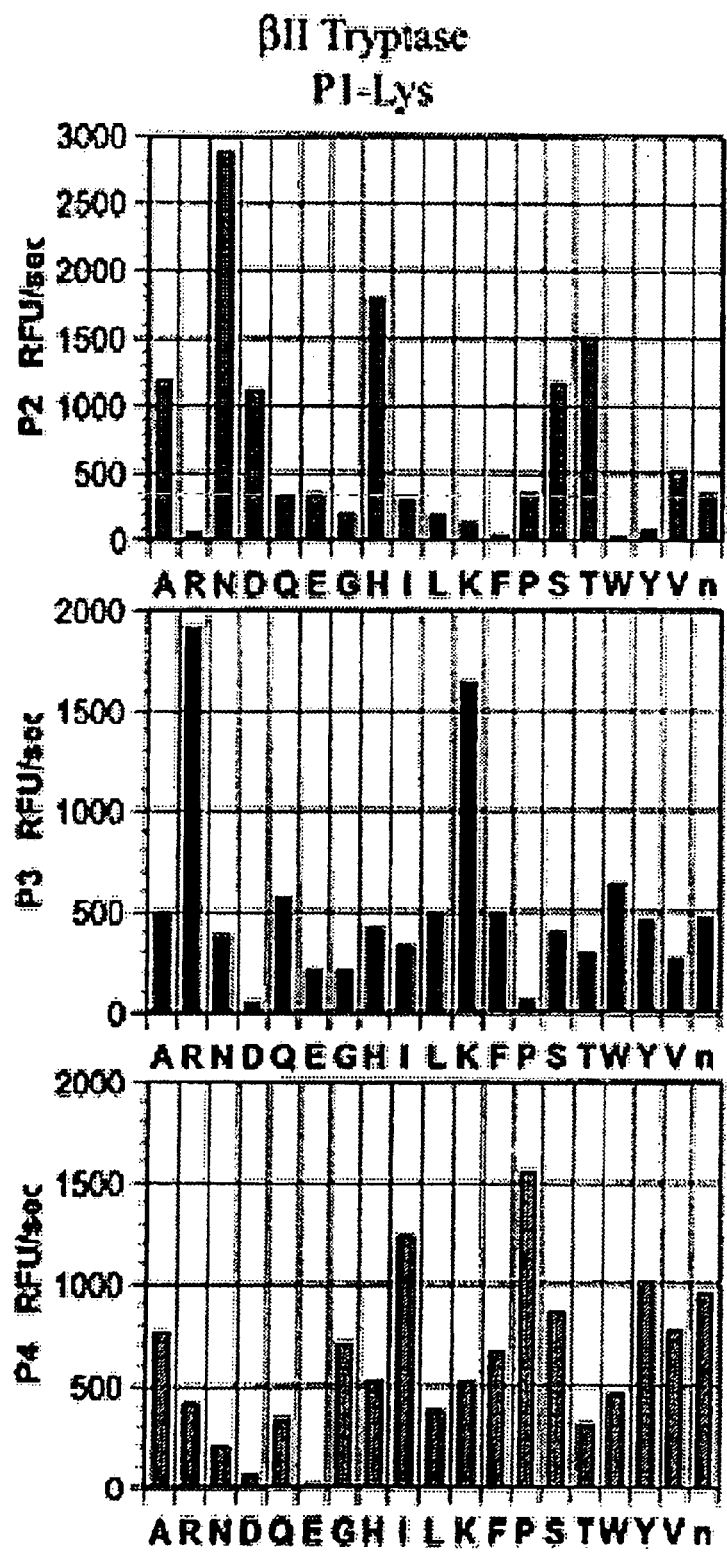
FIGS. 3A and 3B show activity profiles of recombinant human β-I tryptase ("skin tryptase") against P1-fixed Arg or Lys ACC-PS-SCL. These two sets of charts compare the ability of tryptase to cleave a synthetic tetramer wherein the P1 residue is either Lysine (FIG. 3A) or Arginine (FIG. 3B).
Figure 3B:
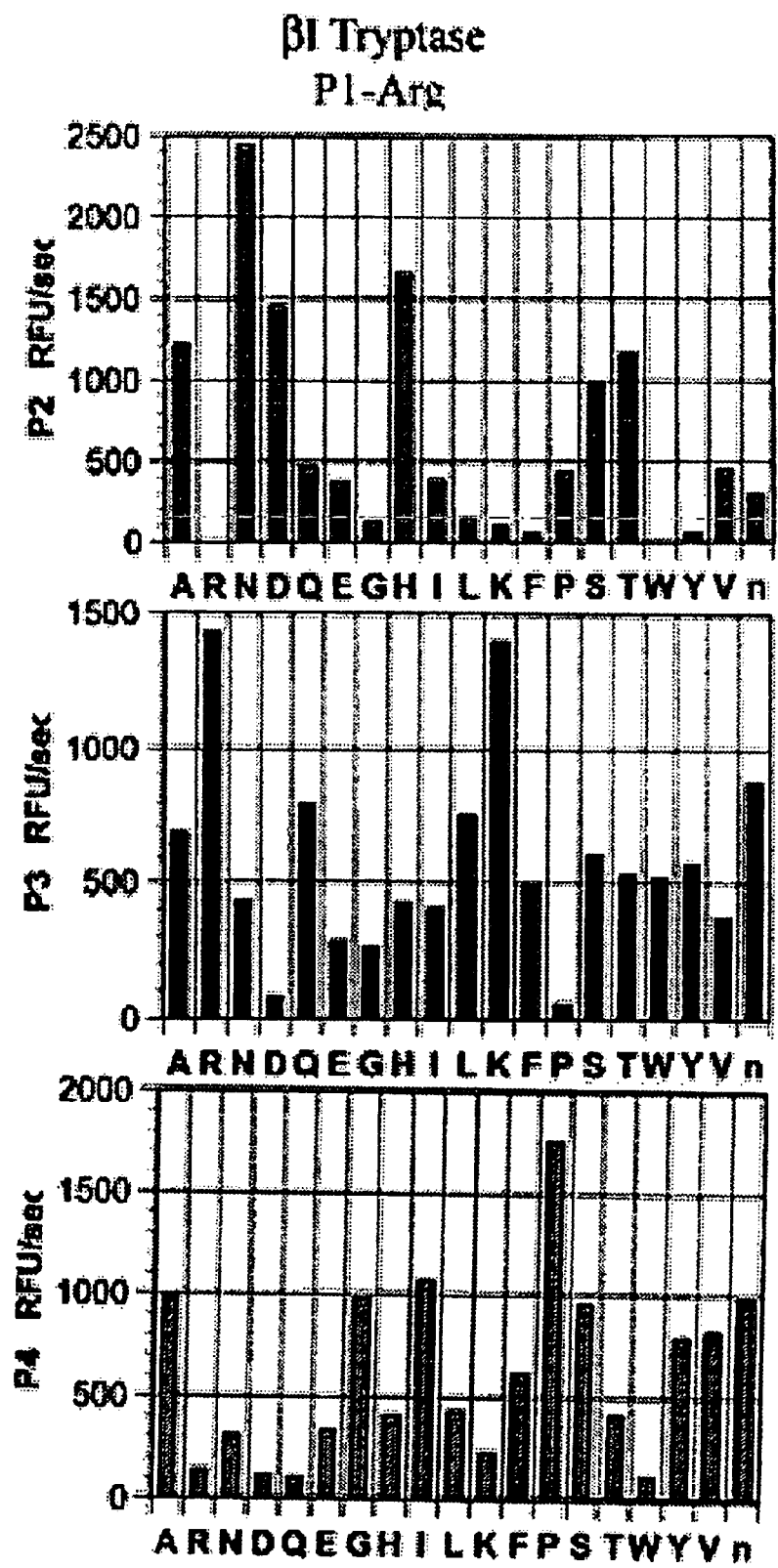
Figure 4A:
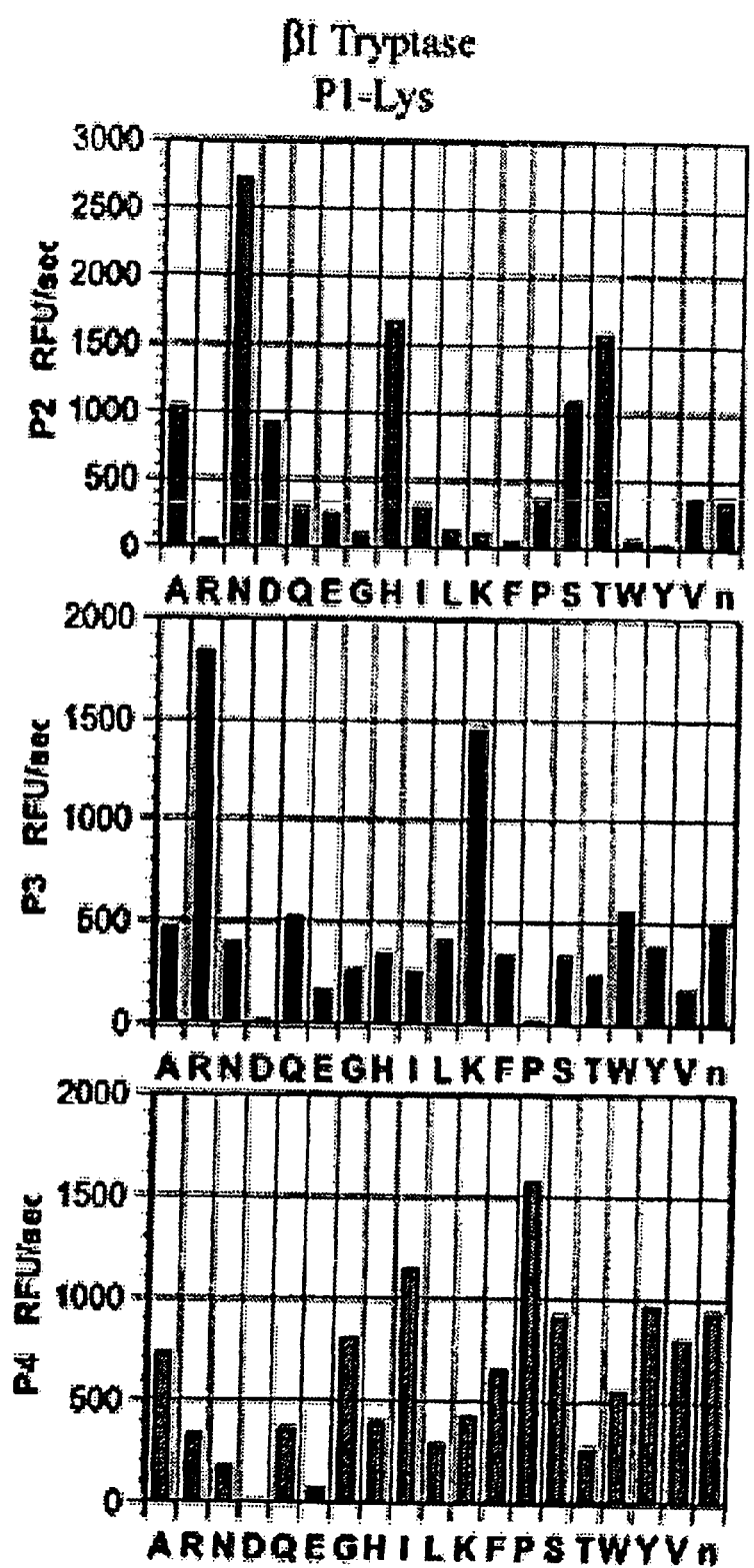
FIGS. 4A and 4B show activity profiles of recombinant human β-II tryptase ("lung tryptase") against P1-fixed Arginine or Lysine ACC-PS-SCL. These two sets of charts compare the ability of tryptase to cleave a synthetic tetramer wherein the P1 residue is either Lysine (FIG. 4A) or Arginine (FIG. 4B).
Figure 4B:
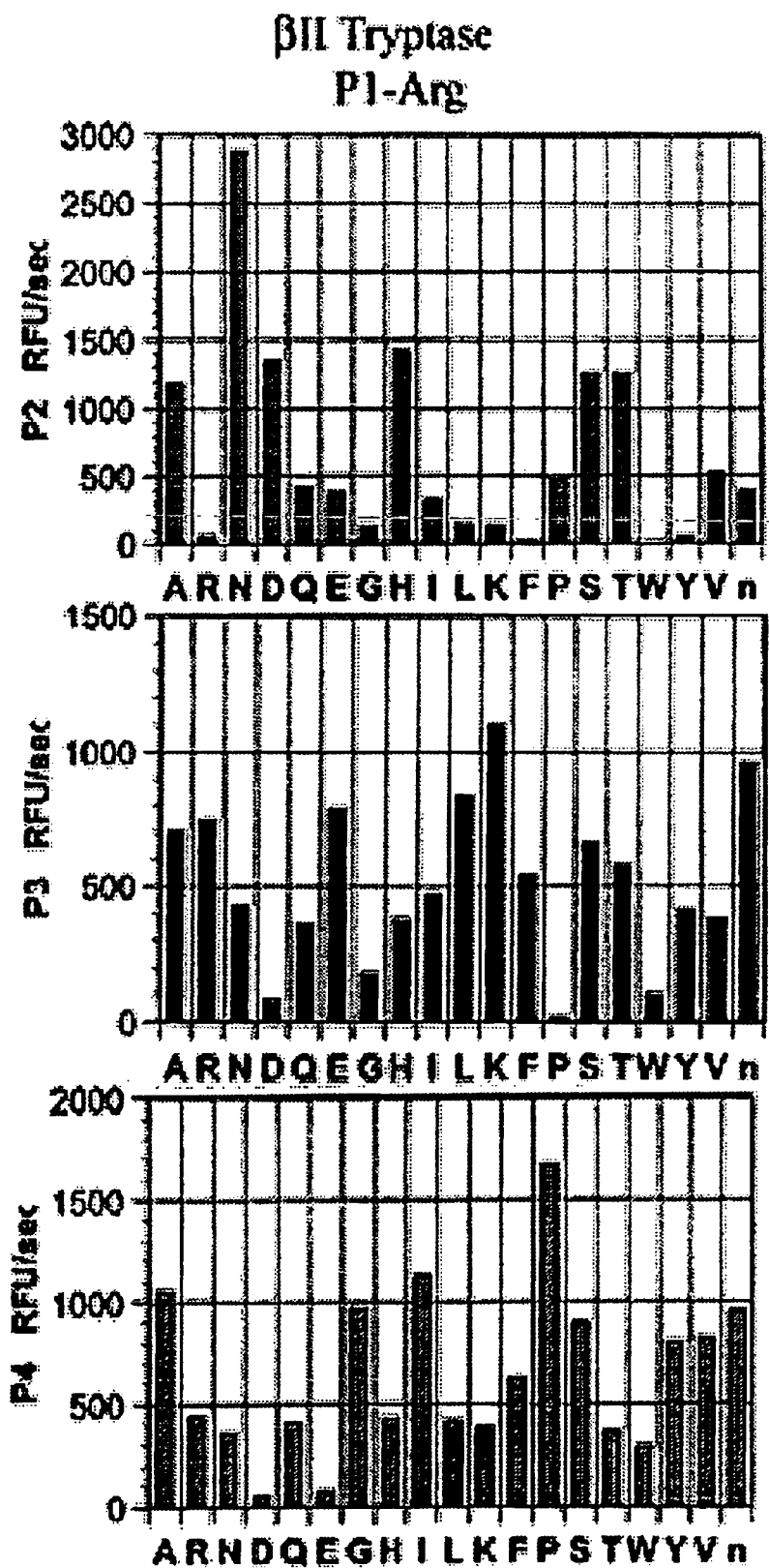

To explore the extended substrate specificities of the β-tryptases as well as to determine if extended specificity was dependent on the context of the P1 amino acid, βI- and βII-tryptases were screened against two libraries that differed only in the P1 amino held constant, lysine and arginine. The P4 to P2 extended substrate specificities of both β-tryptases reveal that the enzymes have a similar substrate preference that is not dependent on whether the P1 amino acid is lysine or arginine (FIGS. 3A and 3B). Also apparent from the specificity screen is that while both enzymes show selectivity at each position, many less optimal amino acids can also be accommodated in the substrate indicating that additional mechanism of substrate discrimination may also be in place. Both tryptases show an unusual preference for proline in the P4 position, no other serine protease screened to date shows this preference. The P3 position shows a preference for positively charged amino acids, lysine and arginine. Finally, the P2-position shows a preference for asparagine (FIGS. 3A and 3B).

Example 4

Kinetic Characterization of Lead Substrates

To quantitate tryptase βI and βII dependence on extended substrate specificity, several peptide substrates were synthesized and the kinetic constants determined for each of the enzymes. The minimal preference for lysine over arginine as seen in the P1-Diverse peptide library was validated with the substrates Ac-PRNK-ACC (SEQ. ID. NO: 12) and Ac-PRNR-ACC (SEQ. ID. NO: 17). The Ac-PRNR-ACC (SEQ. ID. NO: 17) substrate displays about 70–90% of the activity of Ac-PRNK-ACC (SEQ. ID. NO: 12) substrate, compare $k_{cat}/K_m$ of $(1.12\pm0.14)\times10^6 M^{-1}s^{1-}$ to $(1.23\pm0.15)\times10^6 M^{-1}s^{1-}$ for tryptase βI and $(1.31\pm0.19)\times10^6 M^{-1}s^1$ to $(1.89\pm0.17)\times10^6 M^{-1}s^1$ for tryptase βII (Table 2). A minimal preference, approximately 2-fold, for P2-asparagine over P2-threonine was seen for both enzymes when Ac-PRNK-ACC (SEQ. ID. NO: 12) is compared to Ac-PRTK-ACC (SEQ. ID. NO: 16), $k_{cat}/K_m$ of $(0.78\pm0.07)\times10^6 M^{-1}s^1$ to $(1.23\pm0.15)\times10^6 M^{-1}s^1$ for tryptase βI and $(1.27\pm0.12)\times10^6 M^{-1}s^1$ to $(1.89\pm0.17)\times10^6 M^{-1}s^1$ for tryptase βII. A major difference is seen in the P3-position with an approximately 10-fold preference for Ac-PRNK-ACC (SEQ. ID. NO: 12) over Ac-PANK-ACC (SEQ. ID. NO: 15), compare $k_{cat}/K_m$ of $(1.23\pm0.15)\ 10^6 M^{-1}s^1$ to $(0.14\pm0.01)\times10^6 M^{-1}s^1$ for tryptase βI and $(1.89\pm0.17)\times10^6 M^{-1}s^1$ to $(0.18\pm0.01)\times10^6 M^{-1}s^1$ for tryptase βII. All of these effects are manifested in the $K_m$ term, not the $k_{cat}$ term. This indicates that ground state binding and recognition are important factors in tryptase catalysis.

Example 5

Kinetic Comparisons

Table 2 shows a kinetic comparisons of candidate fluorometric tryptase substrates predicted by PS-SCL. Kinetic parameters were independently obtained for both recombinant β-I and β-II tryptases against rational substitutions in the substrates at P2–P4 positions.

TABLE 2

| Substrate | $k_{cat}$ (s$^{-1}$) | $K_m$ (μM) | $k_{cat}/k_m$ (s$^{-1}$M$^{-1}$) |
|---|---|---|---|
| Lung (β-II) Tryptase | | | |
| Ac-PRNK-ACC (SEQ. ID. NO: 12) | 16.84 ± 0.27 | 8.9 ± 0.9 | (1.89 ± 0.17) × 10$^6$ |
| Ac-PANK-ACC (SEQ. ID. NO: 15) | 20.27 ± 0.48 | 110.5 ± 9.8 | (0.18 ± 0.01) × 10$^6$ |
| Ac-PRTK-ACC (SEQ. ID. NO: 16) | 18.67 ± 0.30 | 14.7 ± 1.4 | (1.27 ± 0.12) × 10$^6$ |
| Ac-PRNR-ACC (SEQ. ID. NO: 17) | 21.75 ± 0.67 | 16.5 ± 2.7 | (1.31 ± 0.19) × 10$^6$ |
| Skin (β-I) Tryptase | | | |
| Ac-PRNK-ACC (SEQ. ID. NO: 12) | 17.84 ± 0.40 | 14.5 ± 1.9 | (1.23 ± 0.15) × 10$^6$ |
| Ac-PANK-ACC (SEQ. ID. NO: 15) | 19.06 ± 0.64 | 133.3 ± 15.6 | (0.14 ± 0.01) × 10$^6$ |
| Ac-PRTK-ACC (SEQ. ID. NO: 16) | 18.34 ± 0.33 | 23.4 ± 2.3 | (0.78 ± 0.07) × 10$^6$ |
| Ac-PRNR-ACC (SEQ. ID. NO: 17) | 20.94 ± 0.57 | 18.6 ± 2.6 | (1.12 ± 0.14) × 10$^6$ |

Example 6

AC-PRNK-ACC Exhibits Specificity Against Other Proteins

Figure 5:
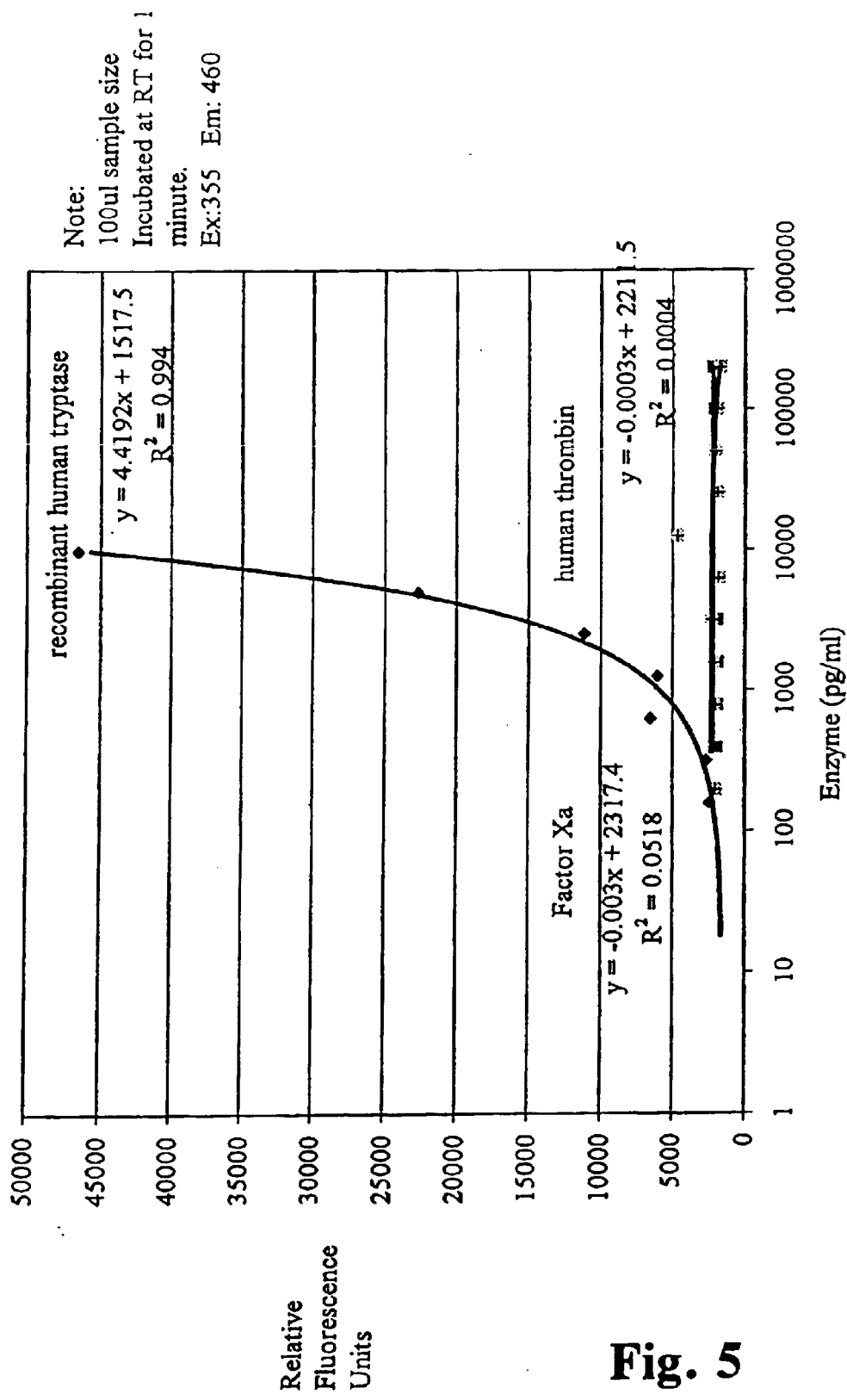
FIG. 5 is a graph showing that Ac-PRNK-ACC (SEQ. ID. NO: 12) is a specific substrate for tryptase in relation to other blood borne serine proteases.

Human recombinant β-I tryptase (Promega) was two-fold serially 25 diluted in triplicate in a microtiter well plate from 10,000 to 156 pg/ml using an "assay buffer" comprised of 100 mM HEPES, 10% v/v glycerol, and 0.1 mg/ml heparin, pH 7.5. Human alpha-thrombin (Haematologic Technologies, Inc.) and bovine factor Xa protease (Promega) were similarly diluted from 200,000 to 190 pg/ml. Ac-PRNK-ACC (SEQ. ID. NO: 12) was added to 100 μM and the plate incubated at room temperature for 1 minute prior to reading at an excitation wavelength of 355 nm and emission wavelength of 460 nm. FIG. 5 shows that Ac-PRNK-ACC (SEQ. ID. NO: 12) is a specific substrate for tryptase in relation to other blood borne serine proteases.

Example 7

Tryptase Activity Over a Broad Protein Range

Human recombinant β-I tryptase (Promega) was two-fold serially diluted in triplicate in a microtiter well plate from 125 to 7.8 ng/ml and 125,000 to 195 pg/ml using an "assay buffer" comprised of 100 mM HEPES, 10% v/v glycerol, and 0.1 mg/ml heparin, pH 7.5. Ac-PRNK-ACC (SEQ. ID. NO: 12) was added to 100 μM and the plate incubated at room temperature for 10 minutes prior to reading at an excitation wavelength of 355 nm and emission wavelength of 460 nm.

Figure 6:
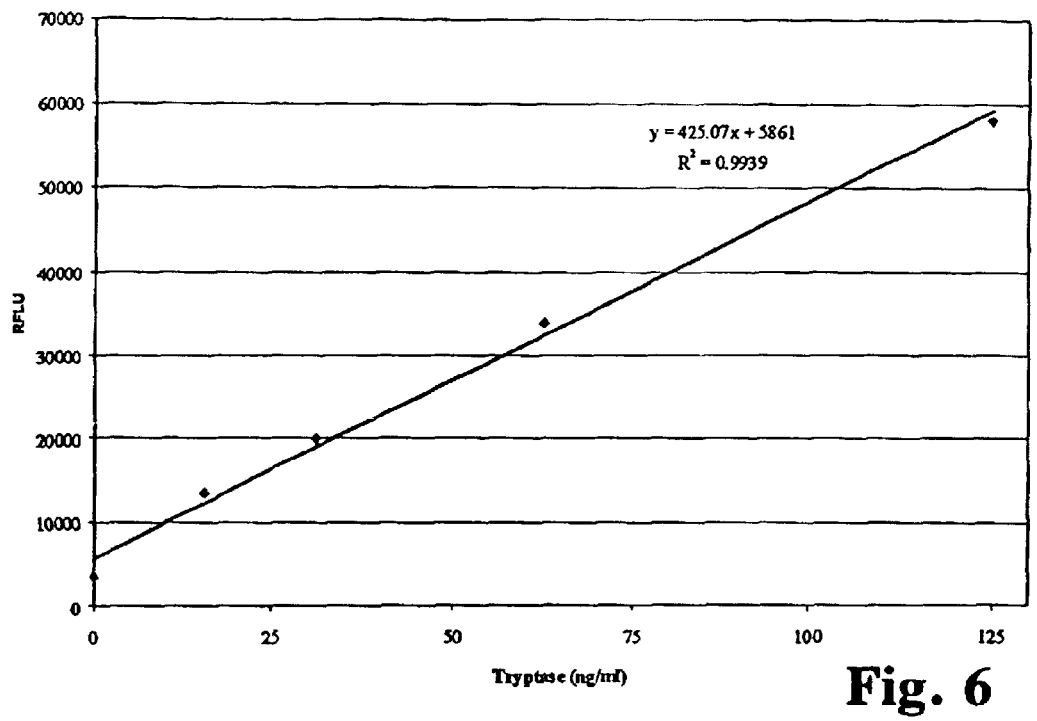
FIGS. 6 and 7 are graphs of typical activity-based standard curves generated using Ac-PRNK-ACC (SEQ. ID. NO: 12) in recombinant tryptase-containing buffer solutions. Curves were generated over a two logarithm tryptase protein concentration range.
Figure 7:
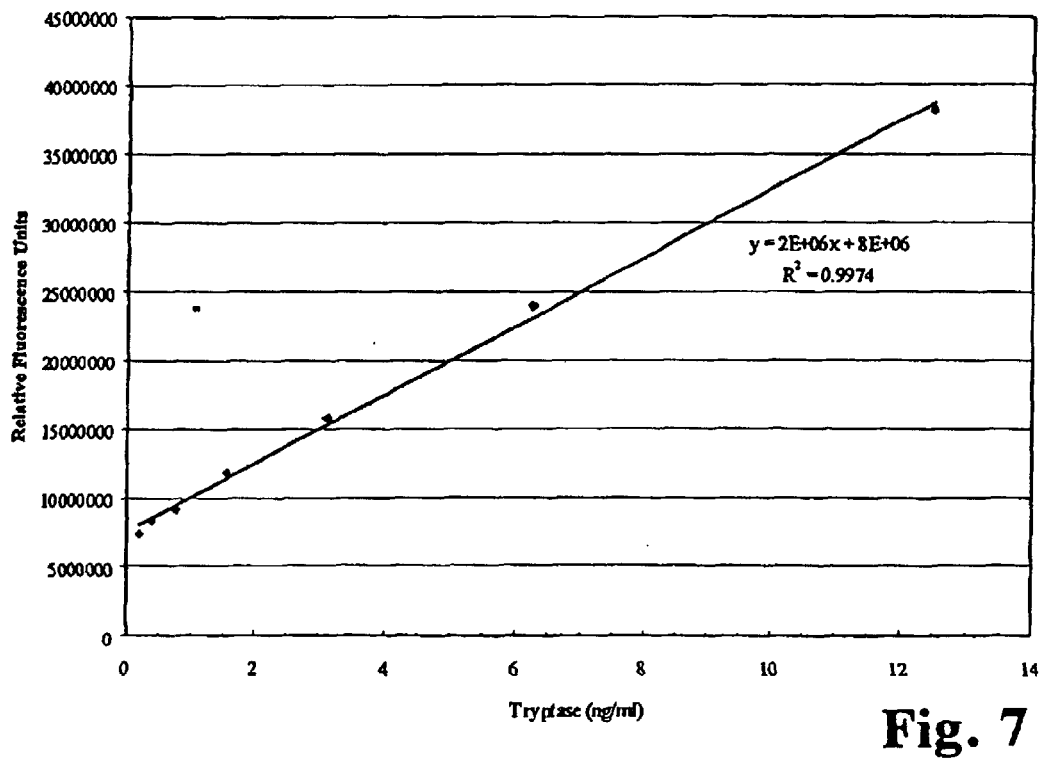

FIGS. 6 and 7 illustrate typical activity-based standard curves generated using Ac-PRNK-ACC (SEQ. ID. NO: 12) in recombinant tryptase-containing buffer solutions. Curves were generated over a two logarithm tryptase protein concentration range.

Example 8

Human β-tryptase Activity in Serum

Human recombinant β-I tryptase (Promega) was two-fold serially diluted in triplicate in a microtiter well plate from 31.25 ng to 0.488 ng/ml in either human serum (Sigma) or a buffer comprised of 100 mM HEPES, 10% v/v glycerol, and 0.1 mg/ml heparin, pH 7.5. Ac-PRNK-ACC (SEQ. ID. NO: 12) was added to 100 μM and the plate incubated at room temperature for 10 minutes prior to reading at an excitation wavelength of 355 nm and emission wavelength of 460 nm.

Figure 8:
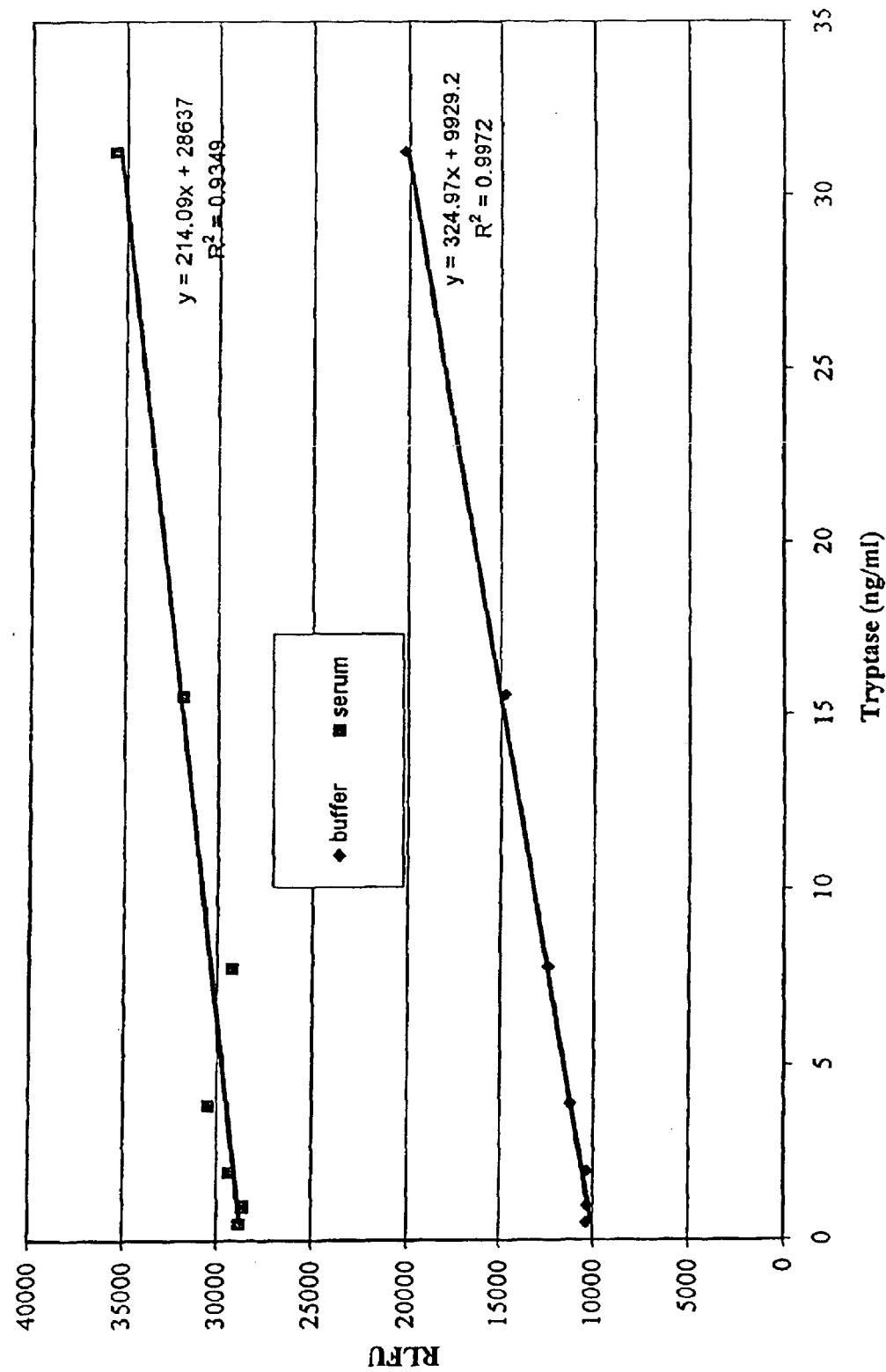
FIG. 8 is a graph showing that linear tryptase standard curves are possible in tryptase-spiked human serum using Ac-PRNK-ACC. Intrinsic fluorescence is consistent across the standard curve.

FIG. 8 demonstrates that linear tryptase standard curves are possible in spiked human serum using Ac-PRNK-ACC (SEQ. ID. NO: 12). Intrinsic fluorescence is consistent across the standard curve.

Example 9

Non-tryptase Proteolytic Activities in Serum

Human recombinant β-I tryptase (Promega) was two-fold serially diluted in human serum from 10,000 pg to 190 pg/ml. Aprotinin, Soybean trypsin inhibitor (SBTI) or antitrypsin was added to each dilution at 25 μg/ml and allowed to incubate at room temperature for 30 minutes. An uninhibited serum standard curve was similarly created. 100 μl of each treated and untreated serum dilution was pipetted in triplicate to a microtiter well plate. Ac-PRNK-ACC (SEQ. ID. NO: 12) was added to 100 μM and the plate incubated at room temperature for 10 minutes prior to reading at an excitation wavelength of 355 nm and emission wavelength of 460 nm.

Figure 9:
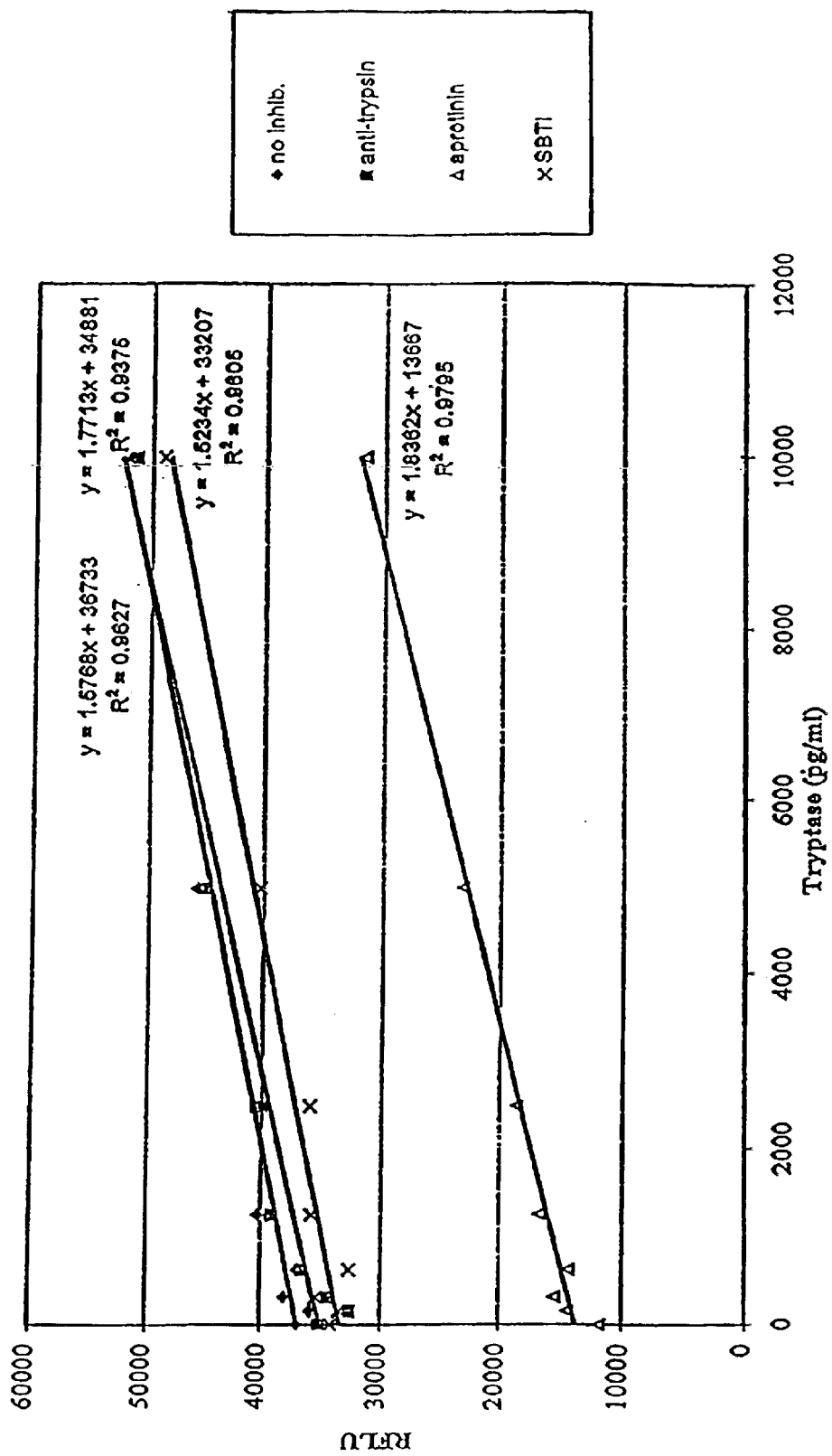
FIG. 9 is a graph showing that the intrinsic fluorescence associated with non-tryptase proteolysis can be significantly and specifically diminished in serum with the serine protease inhibitor, aprotinin.

FIG. 9 shows that intrinsic fluorescence associated with non-tryptase proteolysis can be significantly and specifically diminished in serum with the serine protease inhibitor, aprotinin.

Example 10

Aprotinin Removes Non-tryptase Activity

Figure 10:
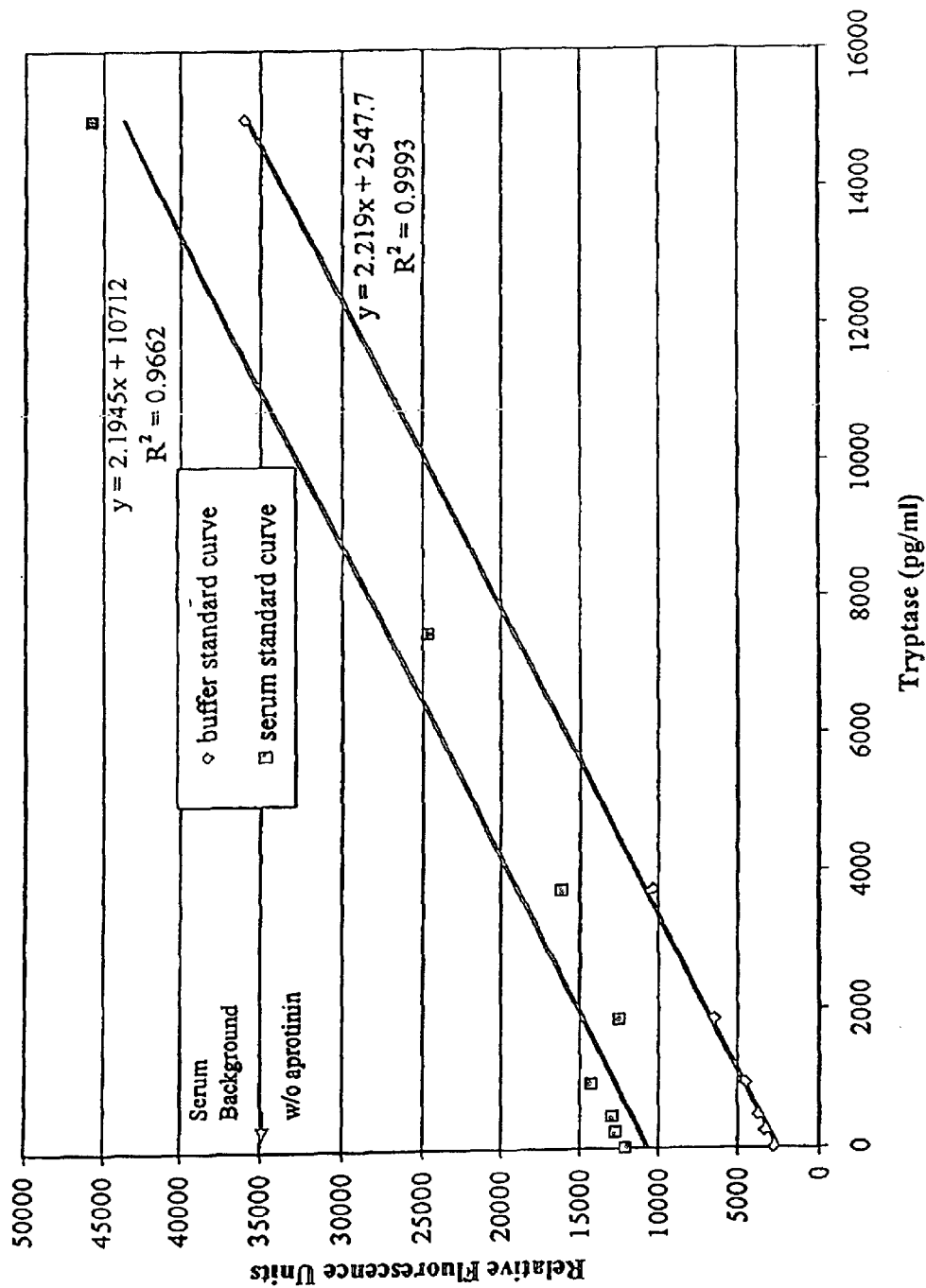
FIG. 10 is a graph showing that linear tryptase standard curves are possible in serum and buffer in the presence of exogenously added aprotinin.

FIG. 10 shows that linear tryptase standard curves are possible in serum and buffer in the presence of exogenously added aprotinin.

The assay was run essentially the same as FIG. 9 with the exception that aprotinin was also added to a human recombinant β-I tryptase buffer standard curve from 15,600 to 237 pg/ml.

Example 11

Tryptase Activity in Urine

Human recombinant β-I tryptase (Promega) was two-fold serially diluted into unfiltered, first-void, normal* human urine from 10,000 pg to 190 pg/ml. Aprotinin was added to a final concentration of 25 μg/ml to one set of the standard concentrations and the solution incubated at room temperature for 30 minutes prior to the addition of Ac-PRNK-ACC (SEQ. ID. NO: 12). The plate was then incubated at room temperature and read at 15 and 30 minutes. "Normal" denotes no history of allergic sensitivities or symptomology.

Figure 11:
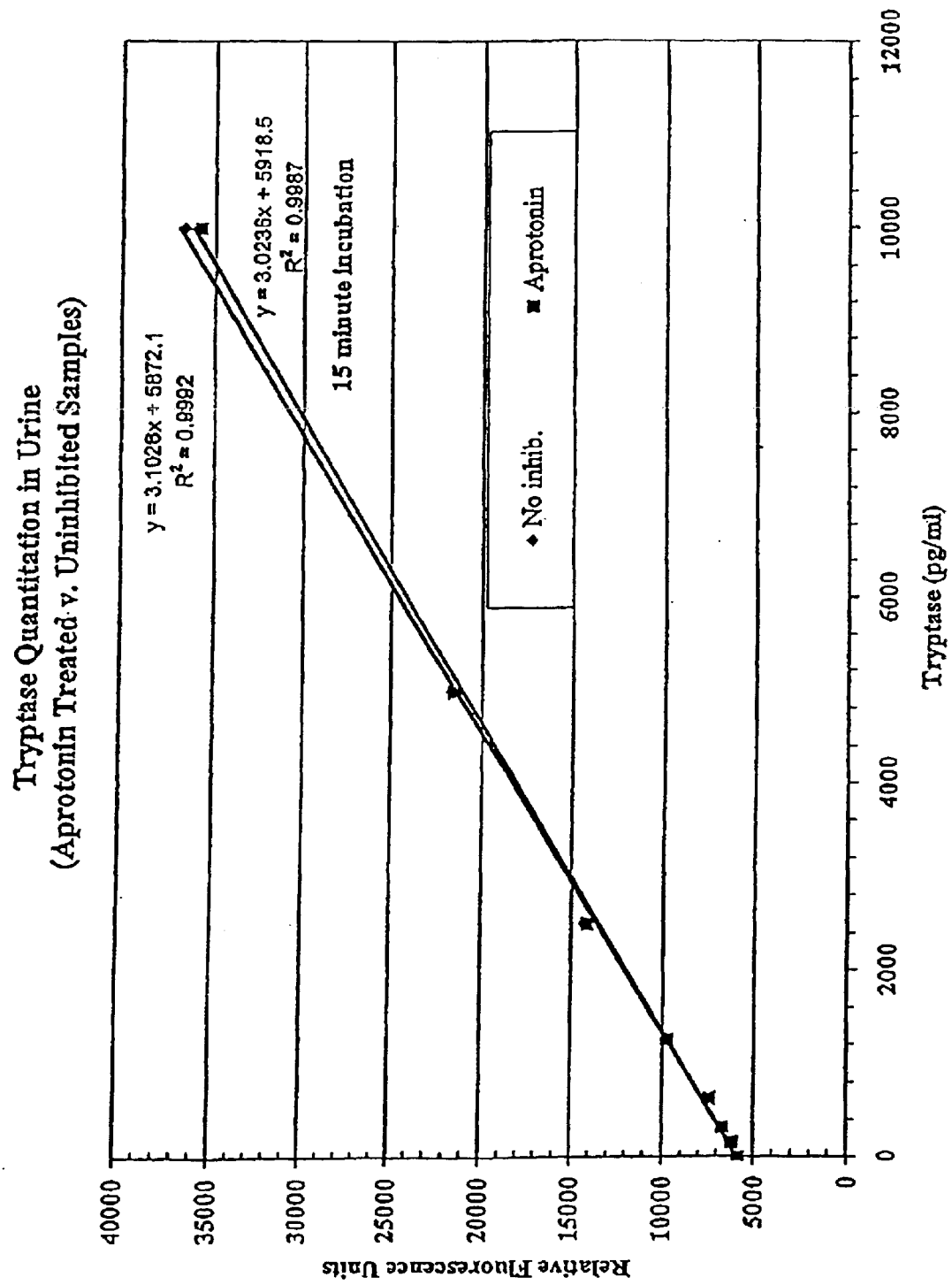
FIG. 11 is a graph showing that linear tryptase standard curves are possible in urine without significant non-tryptase proteolysis. Practical detection limits approach about 300 pg/ml of active tryptase.

FIG. 11 demonstrates that linear tryptase standard curves are possible in urine without significant non-tryptase proteolysis. Practical detection limits nearing 300 pg/ml of active tryptase.

Example 12

Candidate Peptide Coupled with CMK

Ac-PRNK-CMK (SEQ. ID. NO: 14) was two-fold serially diluted from 1000 to 3.9 μM in "assay buffer" consisting of 100 mM HEPES, 10% v/v glycerol, and 0.1 mg/ml heparin, pH 7.5. Human recombinant β-I tryptase (Promega) was added to each tube in 1 μg quantities and allowed to incubate for 30 minutes at room temperature. Kinetic velocity was then determined by the addition of CBZ-Lys-thiobenzyl ester substrate and DNTB to 400 μM and 1 mM final concentrations, respectively, and analysis at 450 nm.

Figure 12:
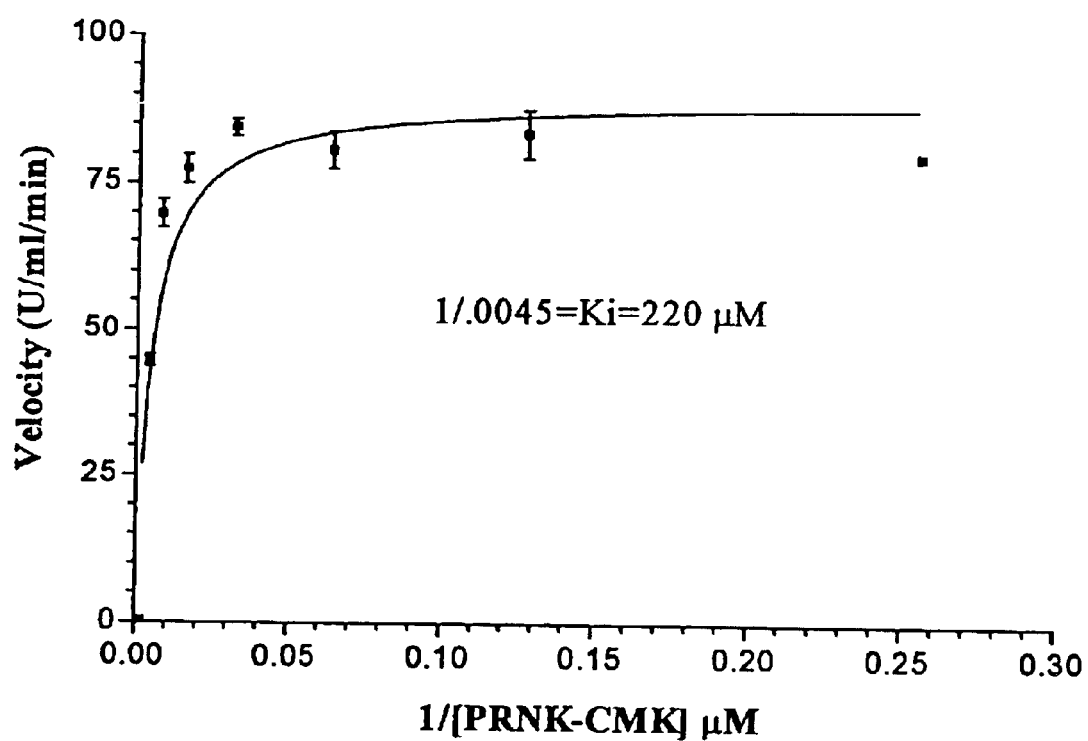
FIGS. 12 and 13 are graphs illustrating that the substituting chloromethyl ketone (CMK) in place of the fluorophore 7-amino-4-carbamoylmethyl-coumarin (ACC) on Ac-PRNK (SEQ. ID. NO: 13) creates an inhibitor of both recombinant human skin (β-I) tryptase (FIG. 12) and recombinant human lung (β-II) tryptase (FIG. 13).
Figure 13:
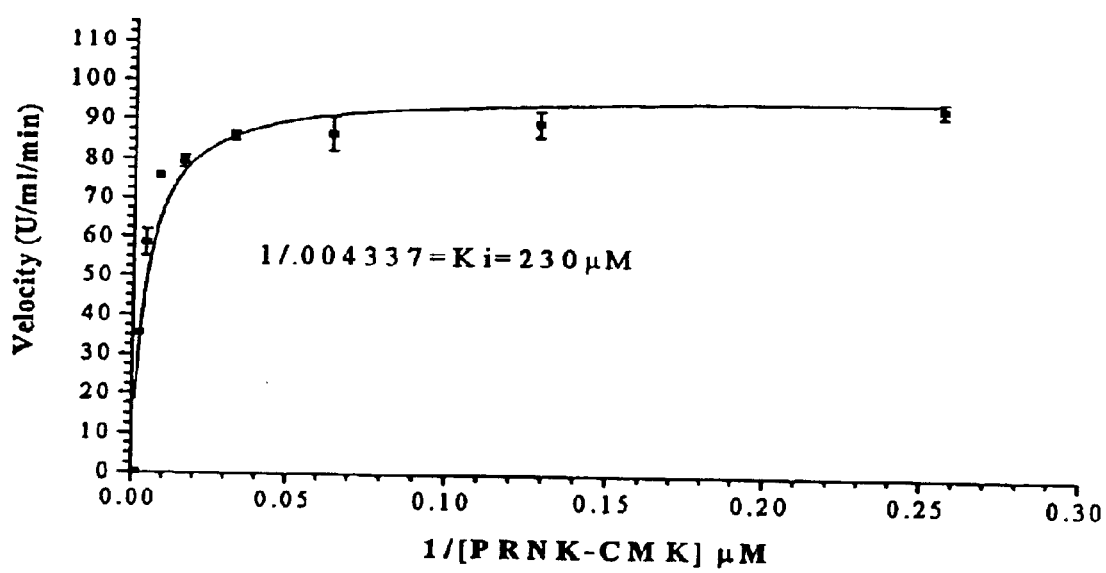

FIGS. 12 and 13 show that the substitution of 7-amino-4-carbamoylmethyl-coumarin (AC C) for chloromethyl ketone (CMK) on Ac-PRNK creates an inhibitor of tryptase isoforms.

Example 13

Candidate Inhibitor Specificity Determination

Ac-PRNK-CMK (SEQ. ID. NO: 14) was two-fold serially diluted from 16130 to 31 μM and 1000 to 31 μM for Factor Xa and thrombin, respectively, in "assay buffer" consisting of 100 mM HEPES, 10% v/v glycerol, and 0.1 mg/ml heparin, pH 7.5. Thrombin was added at 6.6 μg per dilution and factor Xa at 5 μg per dilution. Each set of inhibition dilutions was incubated at room temperature for 30 minutes. Kinetic velocity was then determined by the addition of CBZ-Lys-thiobenzyl ester substrate and DNTB to 400 mM and 1 mM final concentrations, respectively, and analysis at 450 nm.

Figure 14:
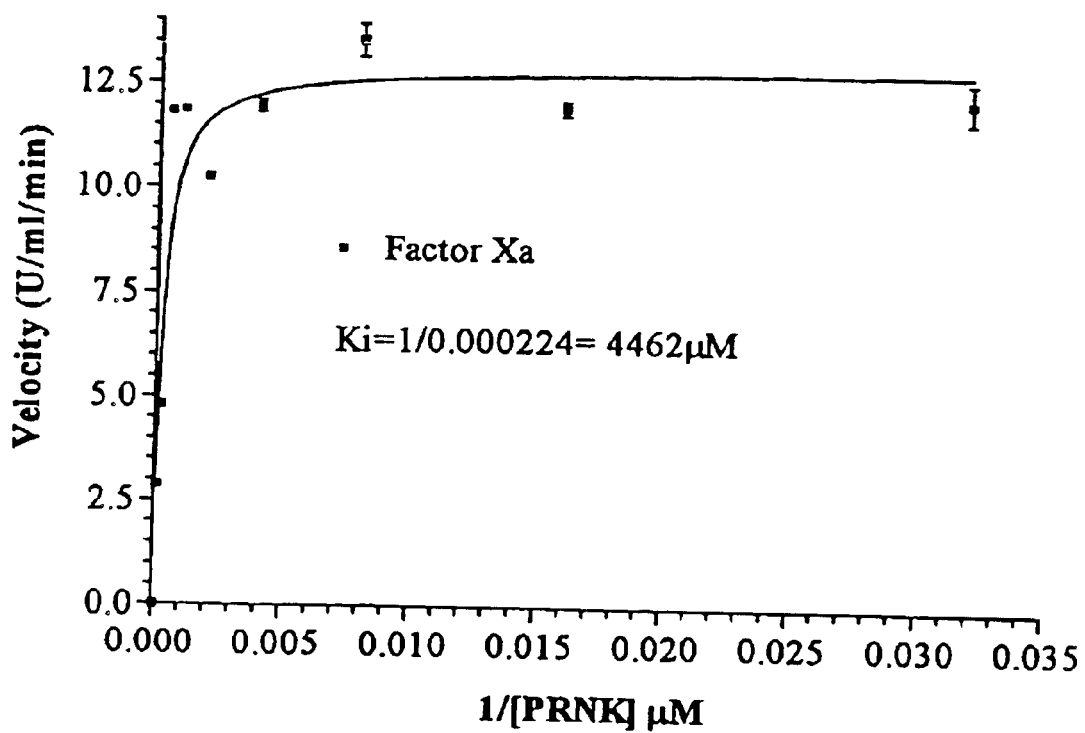
FIG. 14 is a graph demonstrating that the Ac-PRNK-CMK (SEQ. ID. NO: 14) inhibitor is largely ineffective against Factor Xa, a non-tryptase, blood-borne protease with specificity for a certain peptide sequence not fulfilled by PRNK (SEQ. ID. NO: 2).

FIG. 14 illustrates that the Ac-PRNK-CMK (SEQ. ID. NO: 14) inhibitor is largely ineffective against blood borne serine proteases with proteolytic specificity divergent from tryptase, e.g., Factor Xa and thrombin.

Potential/Compelling Physiological Substrates Identified by PS-SCL

Other useful substrates found include the following.

PRTK (SEQ. ID. NO: 7) Latent TGF-b binding protein, Integrin E, methionine aminopeptidase PRFK (SEQ. ID. NO: 19) Pro-urokinase activation site IRSK (SEQ. ID. NO: 20) Granzyme K precursor

SKGR (SEQ. ID. NO: 21) PAR-2

FRTK (SEQ. ID. NO: 22) PAR-2

IKTK (SEQ. ID. NO: 23) Hepatocyte Growth factor

In the same fashion as described above for tryptase, these substrates can be used to assay for the activity of the enzymes listed.

Other enzymes and putatitive corresponding synthetic substrates can be identified by database searching using software such as BLAST. For example, suitable BLAST searches can be done using the following parameters: software: NCBI BlastP 2.0.10; database: non-redundant GenBank CDS; translations, PDB, SwissProt, Spupdate, PIR; advanced search: -e 10,000, -w2.

It is understood that the various preferred embodiments are shown and described above to illustrate different possible features of the invention and the varying ways in which these features may be combined. Apart from combining the different features of the above embodiments in varying ways, other modifications are also considered to be within the scope of the invention. The invention is not intended to be limited to the preferred embodiments described above, but rather is intended to be limited only by the claims set out below Thus, the invention encompasses all alternate embodiments that fall literally or equivalently within the scope of these claims.

BIBLIOGRAPHY

Backes, B. J., Harris, J. L., Leonetti, F., Craik, C. S., and Ellman, J. A. (2000) *Nature Biotechnology* 18(2), 187–193.

Besson, T., Joseph, B., Moreau, P., Viaud, M. C., Coudert, G. & Guillaumet, G. (1992) Heterocycles 34, 273–291.

Bunin, B. A. (1998) The Combinatorial Index (Academic Press, San Diego, Calif.).

Gill, S. C. and von Hippel, P. H. (1989) Anal. Biochem. 182, 319–326.

Harris, J., Backes, B., Leonetti, F., Mabrus, S., Ellman, J., and Craik, C. (2000) *Proceedings of the National Academy of Sciences* 97(14), 7754–7759.

Harris, J. L., Peterson, E. P., Hudig, D., Thornberry, N. A., and Craik, C. S. (1998) *Journal of Biological Chemistry* 273(42), 27364-73.

Huang, C., Li, L., Krilis, S., Chanasyk, K., Tang, Y., Li, Z., Hunt, J., and Stevens, R. (1999) *Journal of Biological Chemistry* 274(28), 19670–19676.

Jameson, G., Roberts, D V, Adams, R W, Kyle, W S, Elmore, D T. (1973) *Biochemical Journal* 131(1), 107–17.

Kanaoka, Y., Kobayashi, A., Sato, E., Nakayama, H., Ueno, T., Muno, D. & Sekine, T. (1984) Chem. Pharm. Bull. 32, 3926–3933.

Lee, D., et al., (1999) *Bioorganic and Medicinal Chemistry Letters* 9:1667–72.

Niles, A. L., Maffitt, M., Haak-Frendscho, M., Wheeless, C. J., and Johnson, D. A. (1998) *Biotechnology and Applied Biochemistry* 28(Pt 2)), 125–31.

Ostresh et al., (1994) Biopolymers 34:1681–1689.

Pallaoro, M., Fejzo, M., Shayesteh, L., Blount, J., and Caughey, G. (1999) *Journal of Biological Chemistry* 274(6), 3355–3362.

Rano, T. A., et al, (1997) Chemistry and Biology 4:149–55.

Sambrook, J.; Fritsch, E. F.; Maniatis, T. (1989), *Molecular Cloning: A Laboratory Manual*; Cold Spring Harbor Laboratory Press: New York, N.Y.

Schwartz, L., Lewis, R., and Austen, K. (1981) *Journal of Biological Chemistry* 256, 11939–11943.

Stack, M., and Johnson, D. (1994) *Journal of Biological Chemistry* 269(13), 9416–9419.

Tam, E., and Caughey, G. (1990) Am. J. Respir. Cell Mol. Biol. 3, 27–32.

---

What is claimed is:

1. An isolated polypeptide comprising in amino to carboxy order P4-P3-P2-P1, wherein P4 is P, P3 is A or R or K, P2 is any amino acid, and P1 is K or R (SEQ. ID. NO: 1 and SEQ. ID. NO: 6), wherein P4 is amino-terminally blocked, and further comprising a fluorogenic leaving group that is covalently bound to P4-P3-P2-P1 at a carboxy-terminus of P4-P3-P2-P1.

2. The isolated polypeptide of claim 1, wherein the fluorogenic leaving group is bound via an amide bond.

3. The isolated polypeptide of claim 1, wherein the fluorogenic leaving group comprises 7-amino-4-carbamoylmethyl-coumarin.

4. The isolated polypeptide of claim 1, wherein P2 is N and further comprising a fluorogenic leaving group that is bound to P4-P3-P2-P1 via an amide bond on a carboxy-terminus of P4-P3-P2-P1.

5. The isolated polypeptide of claim 4, wherein the fluorogenic leaving group comprises 7-amino-4-carbamoylmethyl-coumarin.

6. The isolated polypeptide of claim 3, wherein P4-P3-P2-P1 is selected from the group consisting of P-R-N-K (SEQ. ID. NO: 2), P-K-N-K (SEQ. ID. NO: 3), P-R-N-R (SEQ. ID. NO: 4), P-K-N-R (SEQ. ID. NO: 5), P-A-N-K (SEQ. ID. NO: 6), and P-R-T-K (SEQ. ID. NO: 7).

7. The isolated polypeptide of claim 6, wherein P4-P3-P2-P1 is P-R-N-K (SEQ. ID. NO: 2).

8. The isolated polypeptide of claim 6, wherein P4-P3-P2-P1 is P-K-N-K (SEQ. ID. NO: 3).

9. The isolated polypeptide of claim 6, wherein P4-P3-P2-P1 is P-R-N-R (SEQ. ID. NO: 4).

10. The isolated polypeptide of claim 6, wherein P4-P3-P2-P1 is P-K-N-R (SEQ. ID. NO: 5).

11. The isolated polypeptide of claim 6, wherein P4-P3-P2-P1 is P-A-N-K (SEQ. ID. NO: 6).

12. The isolated polypeptide of claim 6, wherein P4-P3-P2-P1 is P-R-T-K (SEQ. ID. NO: 7).

13. A method of assaying activity of an enzymatically-active β-tryptase in a sample, the method comprising:
  (a) contacting the sample with an isolated polypeptide comprising in amino to carboxy order P4-P3-P2-P1, wherein P4 is amino-terminally blocked and is P, and wherein P4-P3-P2-P1 is selected from the group consisting of P-R-N-K (SEQ. ID. NO: 2), P-K-N-K (SEQ. ID. NO: 3), P-R-N-R (SEQ. ID. NO: 4), P-K-N-R (SEQ. ID. NO: 5), P-A-N-K (SEQ. ID. NO: 6), and P-R-T-K (SEQ. ID. NO: 7), and further wherein a fluorogenic leaving group comprising 7-amino-4-carbamolymethyl-coumarin is bound via an amide bond to P4-P3-P2-P1 at a carboxy-terminus of P4-P3-P2-P1, under conditions wherein an amount of the fluorogenic leaving group is cleaved from P4-P3-P2-P1 upon action of the β-tryptase, thereby producing a fluorescent moiety; and then
  (b) quantifying the amount of detectable leaving group cleaved from the polypeptide, the amount being an indication of the activity of the enzymatically-active β-tryptase in the sample.

14. The method of claim 13, wherein in step (a), the detectable leaving group is a fluorogenic leaving group.

15. The method of claim 14, wherein in step (a), the fluorogenic leaving group is attached to a carboxy-terminus of P4-P3-P2-P1 via an amide bond.

16. The method of claim 14, wherein in step (a), P4 is acetylated.

17. The method of claim 16, wherein in step (b), the amount of detectable leaving group cleaved from the polypeptide is detected by observing whether the sample undergoes a detectable change iii fluorescence.

18. The method of claim 13, wherein the sample is a bodily fluid clinical sample.

19. The method of claim 18, wherein the clinical sample is whole blood, serum, plasma, urine, tears, lavage, tissue extract, or conditioned media.

20. The method of claim 13, further comprising, prior to step (a), adding aprotinin to the sample to inhibit proteases other than β-tryptase, thereby reducing non-specific cleavage of the detectable leaving group from P4-P3-P2-P1 by proteases other than β-tryptase.

21. A method of assaying activity of an euzymatically-active β-tryptase in a sample, the method comprising:
 (a) contacting the sample with an isolated polypeptide comprising in amino to carboxy order P4-P3-F2-P1, wherein P4 is amino-terminally blocked, and wherein P4-P3-P2-P1 is selected from the group consisting of P-R-N-K (SEQ. ID. NO: 2), P-K-N-K (SEQ. ID. NO: 3), P-R-N-R (SEQ. ID. NO: 4), P-K-N-R (SEQ. ID. NO: 5), P-A-N-K (SEQ. ID. NO: 6), and P-R-T-K (SEQ. ID. NO: 7), and further wherein a fluorogenic leaving group comprising 7-amino-4-carbamoylmethyl- coumarin is bound via an amide bond to P4-P3-P2-P1 at a carboxy-terminus of P4-P3-P2-P1, under conditions wherein an amount of the fluorogenic leaving group is cleaved from P4-p3-P2-P1 upon action of the β-tryptase, thereby producing a fluorescent moiety; and then
 (b) measuring whether the sample undergoes a detectable change in fluorescence, the detectable change being an indication of the activity of the enzymatically-active-β-tryptase in the sample.

22. The method of claim 19, further comprising adding aprotinin to the sample to inhibit proteases other than β-tryptase, thereby reducing non-specific cleaveage of the fluorogenic leaving group from P4-P3-P2-P1 by proteases other than β-tryptase.

23. A kit for analyzing samples for β-tryptase activity comprising:
 an isolated polypeptide comprising in amino to carboxy order P4-P3-P2-P1, wherein P4 is P, P3 is A or R or K, P2 is any amino acid, and P1 is K or R (SEQ. ID. NO: 1 and SEQ. ID. NO: 6), and wherein one and only one detectable leaving group is covalently bound to P4-P3-P2-P1, and wherein P4 of the isolated peptide is acylated; and
 a suitable container, the isolated polypeptide being disposed therein.

24. The kit of claim 23, wherein the isolated polypeptide is provided in solution, lyophilized, or bound to a solid support.

25. The kit of claim 23, wherein the detectable leaving group is a fluorogenic leaving group covalently bonded to a carboxy-terminus of P4-P3-P2-P1 via an amide bond.

26. The kit of claim 23, wherein P4-P3-P2-P1 is selected from the group consisting of P-R-N-K (SEQ. ID. NO: 2), P-K-N-K (SEQ. ID. NO: 3), P-R-N-R (SEQ. ID. NO: 4), P-K-N-k (SEQ. ID. NO: 5), P-A-N-K (SEQ. ID. NO: 6), and P-R-T-K (SEQ. ID. NO: 7).

27. A kit for analyzing samples for β-tryptase activity comprising:
 an isolated polypeptide comprising in amino to carboxy order P4-P3-P2-P1, wherein P4 is P, P3 is A or R or K, P2 is any amino acid, and P1 is K or R (SEQ. ID. NO: 1 and SEQ. ID. NO: 6), and wherein zone and oily one detectable leaving group is covalently bound to p4-P3-F2-P1 and
 a suitable container, the isolated polypeptide being disposed therein;
 and further comprising a supply of aprotinin disposed in a second container.

28. The kit of claim 27, wherein the isolated polypeptide is provided in solution, lyophilized, or bound to a solid support.

29. The kit of claim 27, wherein P4 of the isolated polypeptide is acetylated.

30. The kit of claim 27, wherein the detectable leaving group is a fluorogenic leaving group covalently bonded to a carboxy-terminus of P4-P3-P2-P1 via an amide bond.

31. The kit of claim 27, wherein P4-P3-P2-P1 is selected from the group consisting of P-R-N-K (SEQ. ID. NO: 2), P-K-N-K (SEQ. ID. NO: 3), P-R-N-R (SEQ. ID. NO: 4), P-K-N-R (SEQ. ID. NO: 5), P-A-N-K (SEQ. ID. NO: 6), and P-R-T-K (SEQ. ID. NO: 7).

32. A kit for analyzing samples for β-tryptase activity comprising:
 an isolated polypeptide comprising a polypeptide selected from the group consisting of P-R-N-K (SEQ. ID. NO: 2), P-K-N-K (SEQ. ID. NO: 3), P-R-N-R (SEQ. ID. NO: 4), P-K-N-R (SEQ. ID. NO: 5), P-A-N-K (SEQ. ID. NO: 6), and P-R-T-K (SEQ. ID. NO: 7), wherein one and only one detectable leaving group is covalently bound to P4-P3-P2-P1; and
 a suitable container, the isolated polypeptide being disposed therein.

33. The kit of claim 32, wherein the isolated polypeptide is provided in solution, lyophilized, or bound to a solid support.

34. The kit of claim 32, wherein P4 of the isolated polypeptide is acetylated.

35. The kit of claim 32, wherein the detectable leaving group is a fluorogenic leaving group covalently bonded to a carboxy-terminus of P4-P3-P2-P1 via an amide bond.

* * * * *